United States Patent
Krichevsky et al.

(10) Patent No.: US 6,339,143 B1
(45) Date of Patent: Jan. 15, 2002

(54) METHODS OF USING ANTIBODIES AGAINST HORMONE-RELATED DETERMINANTS

(75) Inventors: Alexander Krichevsky, Fox Chapel, PA (US); Steven Birken, Dumont, NJ (US); John O'Connor, New Rochelle; Robert E. Canfield, Cold Spring, both of NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/487,949

(22) Filed: Jun. 7, 1995

(Under 37 CFR 1.47)

Related U.S. Application Data

(63) Continuation of application No. 08/255,482, filed on Jun. 8, 1994, now abandoned, which is a continuation-in-part of application No. 08/219,805, filed on Mar. 29, 1994, now abandoned, and a continuation-in-part of application No. 08/062,925, filed on May 13, 1993, now abandoned.

(51) Int. Cl.$^7$ .............................................. K07K 61/26

(52) U.S. Cl. ............................. 530/388.24; 530/388.1; 435/325; 435/326; 435/336

(58) Field of Search .......................... 530/387.1, 389.2, 530/388.1, 388.24; 435/326, 325, 336

(56) References Cited

U.S. PATENT DOCUMENTS

| | | | |
|---|---|---|---|
| 4,460,561 A | | 7/1984 | Goldenberg et al. |
| 4,565,687 A | * | 1/1986 | Khazaeli et al. ............. 424/1.1 |
| 4,804,626 A | * | 2/1989 | Bellet et al. .................... 435/7 |
| 5,055,559 A | | 10/1991 | Hellstrom et al. |
| 5,445,968 A | * | 8/1995 | Blithe et al. ................ 436/510 |

OTHER PUBLICATIONS

Paul, W. F. (ed.), Fundamental Immunology, 3rd edition, pp. 455–462. Raven Press, New York, 1993.*
Acevedo, Herman F. et al., (1992) Expression of membrane–associated human chorionic gonadotropin, its subunits, and fragments by cultured human cancer cells, *Cancer* 69:7:1829–1842, (Exhibit 6).
Akar, Antoine H. et al., (1988) A radioimmunoassay for the core fragment of the human chorionic gonadotropin β–subunit, *J. of Clin Endo. & Met.* 66:538–545, (Exhibit 7).
Alonso–Whipple, C. et al. (1988) Epitope mapping of human luteinizing hormone using monoclonal antibodies, *Endocrinology* 123:4:1854–1860, (Exhibit 8).
Armstrong, E.G., et al. (1984) Use of a highly sensitive and specific immunoradiometric assay for detection of human chorionic gonadotropin in urine of normal, nonpregnant, and pregnant *J. of Clin. Endo. & Met.* 59:867–874. 1984.

Bellet, D. et al. (1984) A Monoclonal antibody against a synthetic peptide is specific for the free native human chorionic gonadotropin β–subunit, *Endocrinology* 115:1:330–336, (Exhibit 10).
Berger, P. et al. (1988) Antigenic features of human follicle stimulating hormone delineated by monoclonal antibodies and construction of an immuno radiomometric assay, *Endocrinology* 123:5:2351–2359. (Exhibit 11).
Birken, Steven et al. (1991) The heterogeneity of human chorionic gonadotripin (hCG).II. characteristics and origins of nicks in hCG reference standards, *Endocrinology* 129:3:1551–1558, (Exhibit12).
Birken, Steven et al. (1982) Preparation and characterization of an improved β–COOH–terminal immunogen for generation of specific and sensitive antisera to human chorionic gonadotropin, *Endocrinology*, 110:5:1555–1563, (Exhibit 13).
Borrebaeck, Carl A.K., (1989) Strategy for the production of human monoclonal antibodies using in vitro activated B cells, *J. of Immuno. Meth.* 123:157–165, (Exhibit 14).
Caraux, Jean et al. (1985) Non–cross–reactive monoclonal antibodies to human chorionic gonadotropin generated after immunization with a synthetic peptide. *J. of Immunology* 134:2:835–840. (Exibit 16).
Ehrlich, Paul H. et al. (1985) Characterization and relative orientation of epitopes for monoclonal antibodies and antisera to human chorionic gonadotropin, *Am. J. of Reprod. Immuno. and Micro.* 8:48–54, (Exhibit 17).
Ehrlich, Paul H. et al. (1985) Monoclonal antibodies to gonadotropin subunits. In: Birnbaumer, L., O'Malley BW (eds.) *Meth. In Enzymology* part I. Academic Press, New York, 109:638–655, (Exhibit 18).
Fudenberg, Hugh H. et al. (Eds.), "Basic and Clinical Immunology", published 1976 by Lange Medical Pub. 225–241, (Exhibit 19).

(List continued on next page.)

*Primary Examiner*—Sheela Huff
*Assistant Examiner*—Larry R. Helms
(74) *Attorney, Agent, or Firm*—John P. White; Cooper & Dunham LLP

(57) ABSTRACT

This invention provides methods for detecting the presence of human malignant cells in a sample of tumor cells; determining whether a tumor present in a human subject is malignant; obtaining an enriched population of live human malignant cells; determining the amount of intact luteinizing hormone in a sample; determining the ovulatory stage of a subject; determining the amount of intact follicle stimulating hormone in a sample; determining the ovulatory stage of a subject; determining the amount of intact human chorionic gonadotropin in a sample; determining whether a subject is pregnant; determining the ovulatory stage of a subject; determining the amount of free α subunit of human luteinizing hormone in a sample; determining whether a subject has a malignant tumor; determining the amount of nicked human chorionic gonadotropin in a sample; and determining the likelihood of a fetus's being afflicted with Down's syndrome.

4 Claims, 8 Drawing Sheets

OTHER PUBLICATIONS

Hunter, W.M., et al. (1984) A monoclonal antibody–based immunoradiometric assay for h–LH, *Ann. Clin. Biochem.* 21:275–283, (Exhibit 20).

Krichevsky, Alexander et al. (1991) Development and characterization of a new, highly, specific antibody to the human chorionic gonadotropin–β–fragment, *Endocrinology* 128:1:1255–1264, (Exhibit 21).

Krichevsky, Alexander et al. (1988) Preparation and characterization of antibodies to the urinary fragment of the human chorionic gonadotropin β–subunit, *Endocrinology* 123:1:584–593, (Exhibit 22).

Livesy, J.H. et al. (1983) Glycerol prevents loss of immunoreactive follicle–stimulating hormone and luteinizing hormone from frozen urine, *J. of Endocrinology* 98:381–384, (Exhibit 23).

Norman, R.J., et al. (1985) Monoclonal antibodies to human chorionic gonadotropin: implications for antigenic mapping, immunoradiometric assays, and clinical applications, *J. of Clin. Endo. & Met.* 61:6:1031–1038, (Exhibit 24).

O'Connor, John F. et al. (1988) Development of higly of highly sensitive immunoassays to measure human chorionic gonadoropin, its β–subunit, and β core fragment in the urine: application to malignancies, *Cancer Res.* 48:5:1361–1366, (Exhibit 25).

Odell, William D., et al. (1987) Two–monoclonal–antibody "sandwich"–type assay of human lutropin, with no cross reaction with choriogonadotropin. *Clin. Chem.* 33:9:1603–1607, (Exhibit 26).

Paul, William E. (Ed) Fundamental Immunology, 3$^{rd}$ Edition Raven Press, New York, 455–462, 1993 (Exhibit 27).

Pettersson, Kim, Ding, Ying–Qing, and Huhtaniemi, Ilpo, (1991) Monoclonal antibody–based discrepancies between two–site immunometric tests for lutropin, *Clin. Chem.* 37:1745–1748, (Exhibit 28).

Petterson, Kim, Ding, Ying–Qing, and Huhtaniemi, Ilpo, (1992) An immunologically anomalous luteinizing hormone variant in a healthy woman, *Clin. Endo. & Met.* 74:1:164–171, (Exhibit 29).

Raikow, Radmila B. et al. (1987) Flow cytofluorometric analysis of choriogonadotropin–like material on the surface of human and mouse malignant cells, *Can. Det. And Prev.* 1:173–181, (Exhibit 30).

Schwarz, Siegfried, Berger, Peter and Wick, Georg, (1986) The antigenic surface of human chorionic gonadotropin as mapped by murine monoclonal antibodies, *Endocrinology* 118:1:189–197, (Exhibit 31).

Seaver, Sally S. (1994) Monoclonal antibodies in industry: more difficult than originally thought, *Genetic Engineering News* 14:14:10 & 21, (exhibit 32).

Soos, M. et al. (1984) A rapid, sensitive two–site immunometric assay for TSH using monoclonal antibodies: investigation of factors affecting optimization, *J. of Immun.. Meth.* 73:237–249, (Exhibit 33).

Vaidya, H.C., Dietzler, D.N., and Ladenson, J.H. (1985) Inadequacy of traditional ELISA for screening hybridoma supernatants for murine monoclonal antibodies, *Hybridoma* 4:3:271–276, (Exhbit 34).

Vaitukaitis, Judith L., Braunstein, Glenn D. and Ross, Griff T. (1972) A radioimmunoassay which specifically measures human chorionic gonadotropin in the presence of human luteinizing hormone, *Am. J. Obstetrics and Gynecology* 113:6:751–758, (Exhibit 35) and.

Yogeeswaran, G. (1981) The in vitro classical conditioning of the gill withdrawal reflex of aplysia californica. *Am. J. Obslet. Gyn.* 212:1514–1516, (Exhibit 36).

* cited by examiner

METHODS OF USING ANTIBODIES AGAINST HORMONE-RELATED DETERMINANTS

This application is a continuation of U.S. Ser. No. 08/255,482, filed Jun. 8, 1994, now abandoned, which is a continuation-in-part of of U.S. Ser. No. 08/219,805, filed Mar. 29, 1994, now abandonded and a CIP of U.S. Ser. No. 08/062,925, filed May 13, 1993, now abandonded the contents of which are hereby incorporated by reference.

This invention was made with support under Grant Nos. HD 15454 and RR00645 from the National Institutes of Health. Accordingly, the U.S. government has certain rights in the invention.

BACKGROUND OF THE INVENTION

Throughout this application, various publications are referenced. Full citations for these references may be found at the end of the specification immediately preceding the claims. The disclosures of these publications are hereby incorporated by reference into this application to describe more fully the art to which this invention pertains.

The human glycoprotein gonadotropic hormones: luteinizing hormone (hLH), follicle stimulating hormone (hFSH), and chorionic gonadotropin (hCG), are essential for reproduction. These hormones, along with thyroid stimulating hormone (hTSH), are composed of a common $\alpha$ subunit noncovalently combined with a target-specific $\beta$ subunit (Pierce & Parsons, 1981; Hussa, 1987). They appear in blood and urine in a variety of forms ranging from the heterodimeric intact molecules to small fragments (Pierce & Parsons, 1981; Hussa, 1987). All of the glycoprotein hormones are produced by the pituitary, including a small quantity of human chorionic gonadotropin (Hartree et al., 1983), which is primarily a placental product and is excreted in high concentration in first trimester pregnancy urine.

SUMMARY OF THE INVENTION

This invention further provides a method for detecting the presence of human malignant cells in a sample of tumor cells, which comprises contacting the sample with an antibody directed to an epitope present on (i) the $\beta$ subunit of human luteinizing hormone, (ii) the $\beta$ subunit of human chorionic gonadotropin, (iii) intact human luteinizing hormone, or (iv) intact human chorionic gonadotropin, under conditions such that the antibody forms a complex with cells present in the sample if the epitope is present on the surface of the cells, and determining whether the antibody forms such a complex so as to thereby detect the presence of human malignant cells in the sample.

This invention further provides a method for determining whether a tumor present in a human subject is malignant which comprises obtaining a sample of cells from the tumor and detecting the presence of malignant cells in the sample according to the method of the subject invention so as to thereby determine whether the tumor is malignant.

This invention further provides a method for obtaining an enriched population of live human malignant cells which comprises contacting a population of cells comprising live human malignant cells with an antibody directed to an epitope present on (i) the $\beta$ subunit of human luteinizing hormone, (ii) the $\beta$ subunit of human chorionic gonadotropin, (iii) intact human luteinizing hormone, or (iv) intact human chorionic gonadotropin, under conditions such that the antibody forms a complex with the cells present in the population if the epitope is present on the surface of the cells, and isolating the cells which form a complex with the antibody so as to obtain an enriched population of live human malignant cells.

This invention further provides a method for determining the amount of intact luteinizing hormone in a sample which comprises contacting the sample with a suitable amount of antibody directed to an epitope present only on intact luteinizing hormone under conditions permitting the formation of a complex between the antibody and the epitope, determining the amount of complex so formed, and comparing the amount of complex so formed to a known standard so as to thereby determine the amount of intact luteinizing hormone in the sample.

This invention further provides a method for determining the ovulatory stage of a subject which comprises obtaining a suitable sample from the subject, determining the amount of intact luteinizing hormone in the sample according to the method of the subject invention, and comparing the amount of intact luteinizing hormone so determined to a known standard so as to determine the ovulatory stage of the subject.

This invention further provides a method for determining the amount of intact follicle stimulating hormone in a sample which comprises contacting the sample with a suitable amount of antibody directed to an epitope present on intact follicle stimulating hormone under conditions permitting the formation of a complex between the antibody and the epitope, determining the amount of complex so formed, and comparing the amount of complex so formed to a known standard so as to thereby determine the amount of intact follicle stimulating hormone in the sample.

This invention further provides a method for determining the ovulatory stage of a subject which comprises obtaining a suitable sample from the subject, determining the amount of intact follicle stimulating hormone in the sample according to the method of the subject invention, and comparing the amount of intact follicle stimulating hormone so determined to the amount of intact follicle stimulating hormone present in a sample from a subject at a known ovulatory stage so as to determine the ovulatory stage of the subject.

This invention further provides a method for determining the amount of intact human chorionic gonadotropin in a sample which comprises contacting the sample with a suitable amount of antibody directed to an epitope present only on intact human chorionic gonadotropin under conditions permitting the formation of a complex between the antibody and the epitope, determining the amount of complex so formed, and comparing the amount of complex so formed to a known standard so as to thereby determine the amount of intact human chorionic gonadotropin in the sample.

This invention further provides a method for determining whether a subject is pregnant which comprises obtaining a suitable sample from the subject, determining the amount of intact human chorionic gonadotropin in the sample according to the method of the subject invention, and comparing the amount of intact human chorionic gonadotropin so determined to a known standard so as to determine whether the subject is pregnant.

This invention further provides a method for determining the ovulatory stage of a subject which comprises obtaining a suitable sample from the subject, determining the amount of intact human chorionic gonadotropin in the sample according to the method of the subject invention, and comparing the amount of intact human chorionic gonadotropin so determined to the amount of intact human chorionic gonadotropin present in a sample from a subject at a known ovulatory stage so as to determine the ovulatory stage of the subject.

This invention further provides a method for determining the amount of free α subunit of human luteinizing hormone in a sample which comprises contacting the sample with a suitable amount of antibody directed to an epitope present on the a subunit of human luteinizing hormone under conditions permitting the formation of a complex between the antibody and the epitope, determining the amount of complex so formed, and comparing the amount of complex so formed to a known standard so as to thereby determine the amount of free α subunit of human luteinizing hormone in the sample.

This invention further provides a method for determining whether a subject has a malignant tumor which comprises obtaining a suitable sample from the subject, determining the amount of free α subunit of human luteinizing hormone in the sample according to the method of the subject invention, and comparing the amount of free α subunit of human luteinizing hormone so determined to a known standard so as to determine whether the subject has a malignant tumor.

This invention further provides a method for determining the amount of nicked human chorionic gonadotropin in a sample which comprises contacting the sample with a suitable amount of antibody which preferentially binds to an epitope present only on nicked human chorionic gonadotropin under conditions permitting the formation of a complex between the antibody and the epitope, determining the amount of complex so formed, and comparing the amount of complex so formed to a known standard so as to thereby determine the amount of nicked human chorionic gonadotropin in the sample.

This invention further provides a method for determining whether a subject is pregnant which comprises obtaining a suitable sample from the subject, determining the amount of nicked human chorionic gonadotropin in the sample according to the method of the subject invention, and comparing the amount of nicked human chorionic gonadotropin so determined to an amount of nicked human chorionic gonadotropin correlative with a known state of pregnancy so as to determine whether the subject is pregnant. In the preferred embodiment, the suitable sample is a urine sample.

This invention further provides a method for determining whether a subject has a malignant tumor which comprises obtaining a suitable sample from the subject, determining the amount of nicked human chorionic gonadotropin in the sample according to the method of the subject invention, and comparing the amount of nicked human chorionic gonadotropin so determined to a known standard so as to determine whether the subject has a malignant tumor. In the preferred embodiment, the suitable sample is a urine sample.

Finally, this invention provides a method for determining the likelihood of a fetus's being afflicted with Down's syndrome which comprises obtaining a suitable sample from the mother of the fetus, determining the ratio of the amount of free human chorionic gonadotropin β subunit in the sample to the amount of intact human chorionic gonadotropin in the sample, and comparing the ratio so determined to a known standard so as to determine the likelihood of the fetus's being afflicted with Down's syndrome.

Cartoon illustrating the epitope map for antibodies of hLH. The relative locations of seven antibody-binding regions (cross-hatched circles enumerated by roman numerals) based on the ability of antibodies to bind simultaneously (different sites) or inhibit each other from binding (same sites). Details of the site assignments are described in the text. The numbering of sites starts from Site II because Site I was used earlier to designate the COOH-terminal terminal related binding region on hCG (Ehrlich et al., 1985; Norman et al., 1985). This region is absent from hLH.

FIG. 2

This Figure illustrates a representative menstrual cycle from a normal woman who did not become pregnant during the cycle. First, morning urine was collected with glycerol as a cryoprotectant (0.76 ml/20 ml urine). Daily assays were performed for intact hLH and hLH free β subunit. Both molecular forms show clear mid-cycle preovulatory peaks. Daily measurements of pregnanediol-3-glucuronide were also performed to confirm that ovulation had occurred. All measurements have been normalized to creatinine.

FIG. 3

Dose-response curves performed with antibodies CTP-101, CTP-102, and CTP-103 using $[^{125}I]$hCG as tracer and hCG or synthetic βCTP-(111–145) as competitors. The molar concentration of competitor solutions appear on the x-axis, and the logit percent bound of radiolabeled hCG appears on the y-axis.

FIG. 4

Figure 3:
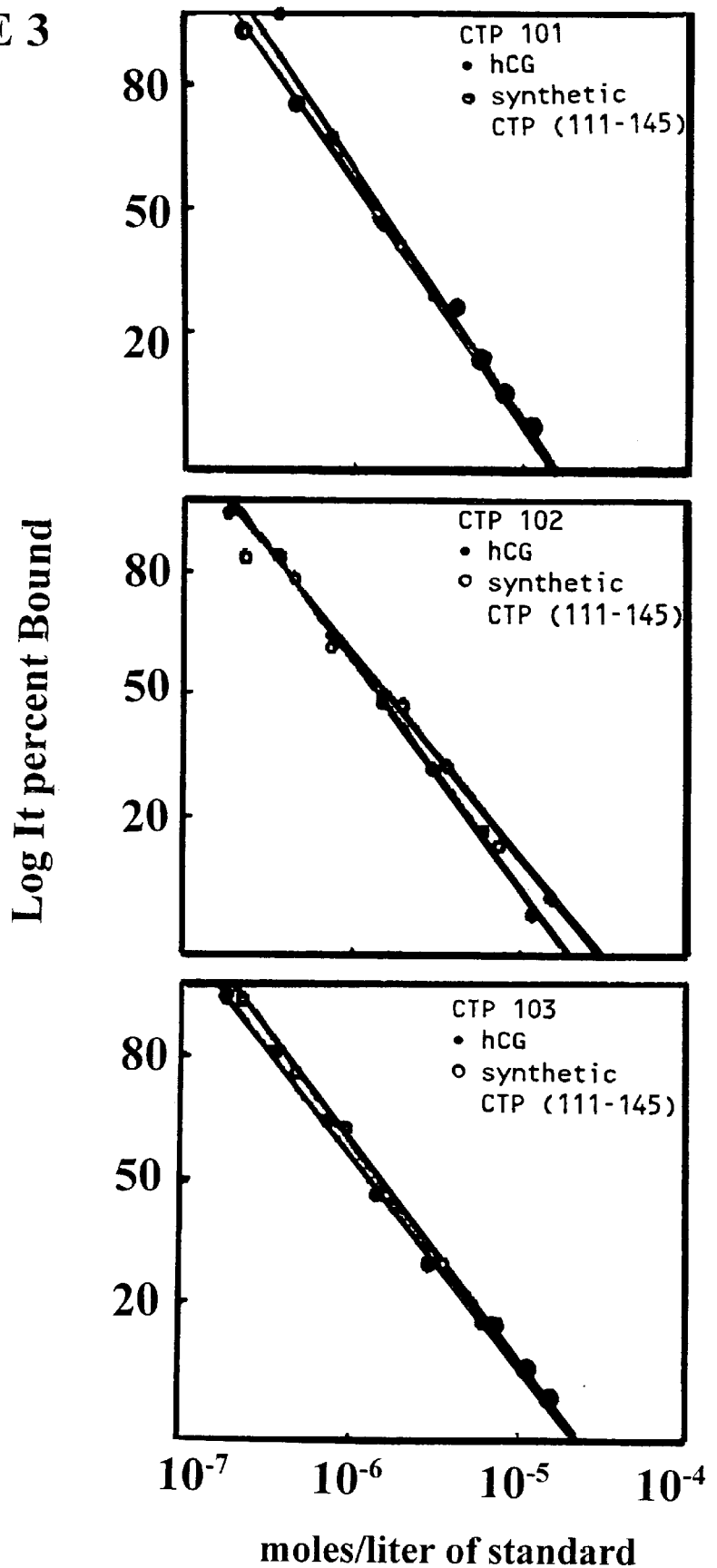

Dose-response curves of antibodies CTP-104 and CTP-105 with [125I]hCG as tracer and hCG, synthetic β-(111–145) and β-(122–145), as well as desialylated hCG as competitors. Axes are explained in FIG. 3.

FIG. 5

Western blot of nonreduced SDS-gels of hCG CR127 (1) and desialylated CR127 (2). The band at 43 kDa represents hCG (1), whereas the lower band at 33 kDa represents some dissociated hCG β-subunit. Nitrocellulose was stained with the BCTP antibody denoted below each blot. Mol. wt. standards appear at the extreme left.

FIG. 6

Western blot of reduced SDS-gel of hCG (CR127) (2) and increasing concentrations of crude pituitary extract (3-5). The nitrocellulose was stained with antibody CTP-103. Lane 1 represents mol wt (MW) markers. The 20 kDa lower band in lane 2 represents β-(45–145) and β-(48–145) resulting from known peptide bond cleavages in hCG reference preparations. The band at 33 kDa is intact hCGB. Note that the pituitary extract, even at high concentration (lane 5), does not display any of the significant peptide bond cleavage that is found in hCG circulating in blood or excreted in urine (24, 25).

Figure 7A:
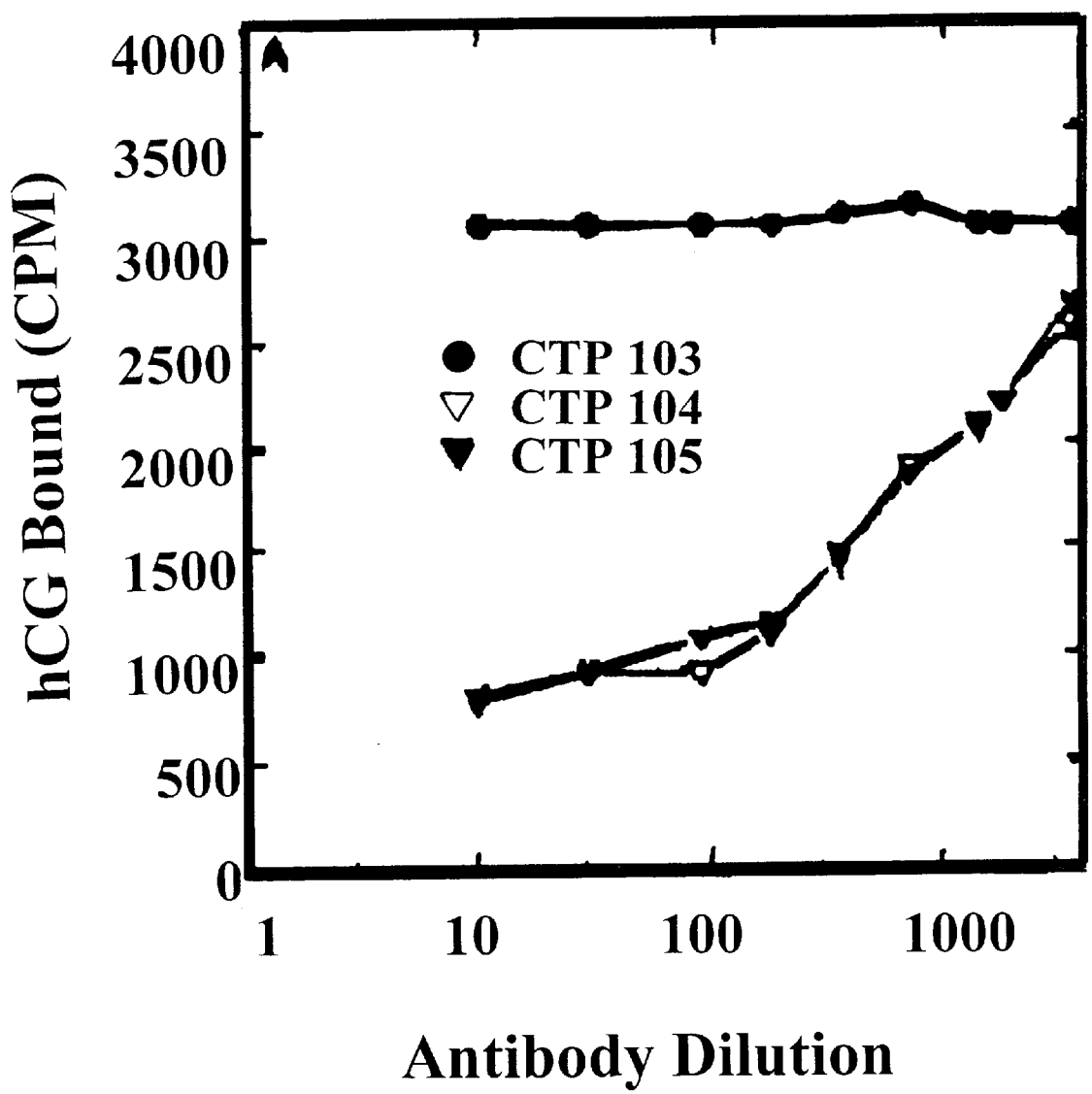
Figure 7B:
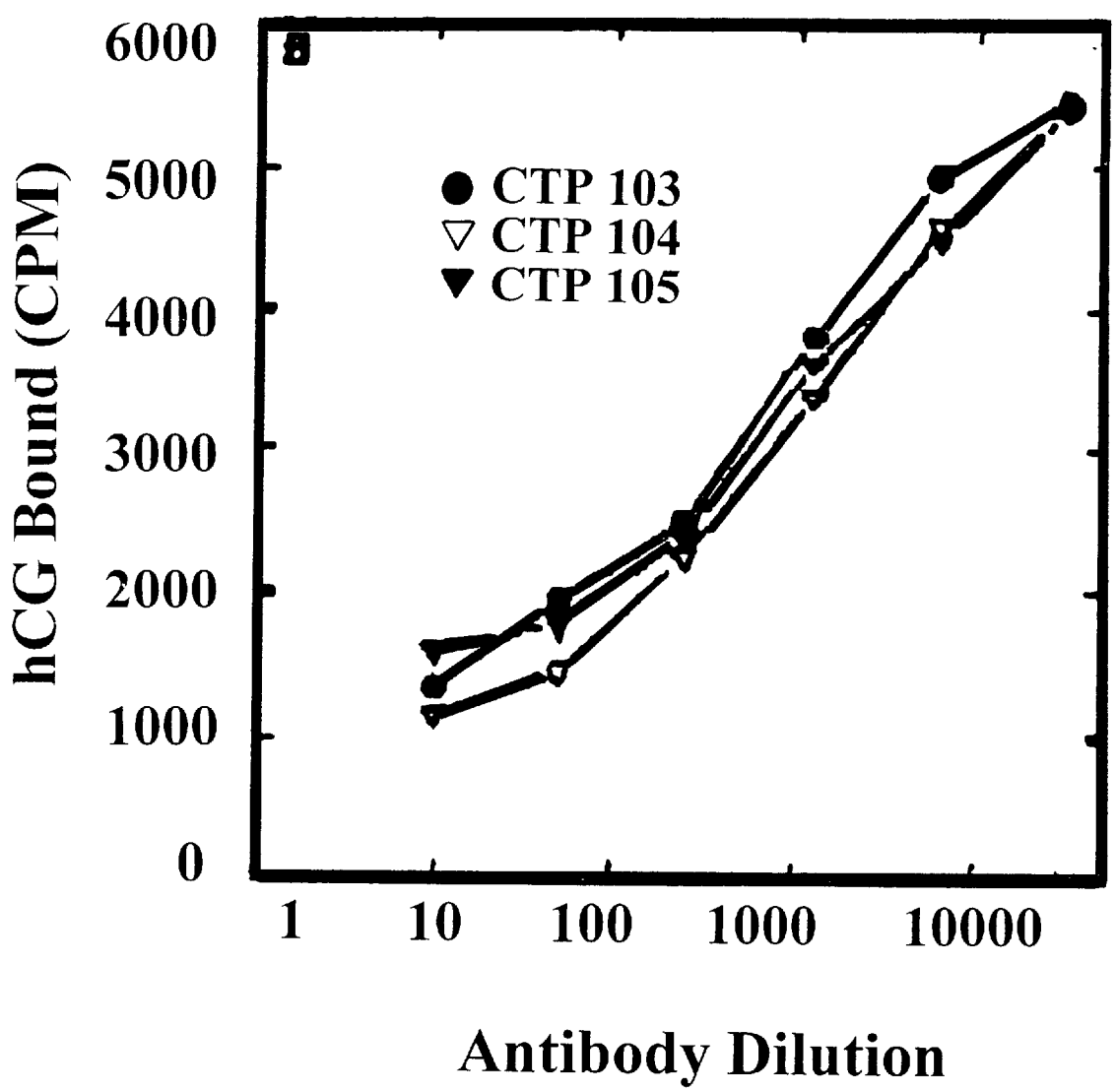

FIGS. 7A and 7B

Competition experiments between monoclonal antibodies (MABs) CTP-(1030105) and rabbit monoclonal antibodies. The x-axis shows dilution of monoclonal antibody competitors. The y-axis is the counts of $[^{125}I]$hCG bound to the rabbit antiserum. A, Rabbit βCTP antiserum R561; B, rabbit antiserum R525. It is known that R561 is a hCG-sialic-acid requiring antiserum (9) and that CTP-104 and CTP-105 have the same requirement for this sugar as well as for the βCTP primary structure. These two antibodies compete with R561 for binding to $[^{125}I]$hCG (A) and inhibit R561 from binding, showing that they are all directed to a common site on the βCTP, whereas CTP-103 is not inhibitory and does not compete for this antibody site. In contrast, all three CTP antibodies compete for the βCPT site recognized by R525 on hCG (B). The latter is the most common carbohydrate-independent epitope on βCTP.

DETAILED DESCRIPTION OF THE INVENTION

This invention provides an antibody directed to an epitope present on the β subunit of human luteinizing hormone. In one embodiment, the antibody is a monoclonal antibody. The monoclonal antibody may be the monoclonal antibody designated B408, B409, B411 or B412.

As used in the subject invention, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof.

This invention further provides a hybridoma cell line capable of producing a monoclonal antibody directed to an epitope present on the β subunit of human luteinizing hormone. The hybridoma cell line may be the hybridoma cell line producing the monoclonal antibody designated B408, B409, B411 or B412.

This invention further provides an antibody directed to an epitope present on the β subunit of human chorionic gonadotropin. In one embodiment, the antibody is a monoclonal antibody. The monoclonal antibody may be the monoclonal antibody designated B411, B412, CTP101, CTP102, CTP103, CTP104 or CTP105.

This invention further provides a hybridoma cell line capable of producing a monoclonal antibody directed to an epitope present on the β subunit of human chorionic gonadotropin. The hybridoma cell line may be the hybridoma cell line producing the monoclonal antibody designated B411, B412, CTP101, CTP102, CTP103, CTP104 or CTP105.

This invention further provides an antibody directed to an epitope present on intact luteinizing hormone. In one embodiment, the antibody is a monoclonal antibody. The monoclonal antibody may be the monoclonal antibody designated B413.

This invention further provides a hybridoma cell line capable of producing a monoclonal antibody directed to an epitope present on intact luteinizing hormone. The hybridoma cell line may be the hybridoma cell line producing the monoclonal antibody designated B413.

As used herein, an "epitope present on intact luteinizing hormone" means an epitope which is formed by the juxtaposition of the α and β subunit s of luteinizing hormone, and which exists only on the intact luteinizing hormone comprising the α and β subunits.

This invention further provides an antibody directed to an epitope present on intact human luteinizing hormone. In one embodiment, the antibody is a monoclonal antibody. In the preferred embodiment, the monoclonal antibody is the monoclonal antibody designated B405, B406 or B407.

This invention further provides a hybridoma cell line capable of producing a monoclonal antibody directed to an epitope present on intact human luteinizing hormone. The hybridoma cell line may be the hybridoma cell line producing the monoclonal antibody designated B405, B406 or B407.

This invention further provides an antibody directed to an epitope present on intact human chorionic gonadotropin. In one embodiment, the antibody is a monoclonal antibody. The monoclonal antibody may be the monoclonal antibody designated B407.

This invention further provides a hybridoma cell line capable of producing a monoclonal antibody directed to an epitope present on intact human chorionic gonadotropin. The hybridoma cell line may be the hybridoma cell line producing the monoclonal antibody designated B407.

As used herein, an "epitope present on intact human chorionic gonadotropin" means an epitope which is formed by the juxtaposition of the α and β subunit s of human chorionic gonadotropin, and which exists only on the intact human chorionic gonadotropin comprising the α and β subunits.

This invention further provides an antibody directed to an epitope present on intact follicle stimulating hormone. In one embodiment, the antibody is a monoclonal antibody. The monoclonal antibody may be the monoclonal antibody designated FSH-101.

This invention further provides a hybridoma cell line capable of producing a monoclonal antibody directed to an epitope present on intact follicle stimulating hormone. The hybridoma cell line may be the hybridoma cell line producing the monoclonal antibody designated FSH-101.

As used herein, an "epitope present on intact follicle stimulating hormone" means an epitope which is formed by the juxtaposition of the α and β subunit s of follicle stimulating hormone, and which exists only on the intact follicle stimulating hormone comprising the α and β subunits.

This invention further provides an antibody directed to an epitope present on the α subunit of human luteinizing hormone. In one embodiment, the antibody is a monoclonal antibody. The monoclonal antibody may be the monoclonal antibody designated A501, A502, A201 or A202.

This invention further provides a hybridoma cell line capable of producing a monoclonal antibody directed to an epitope present on the α subunit of human luteinizing hormone. The hybridoma cell line may be the hybridoma cell line producing the monoclonal antibody designated A501, A502, A201 or A202.

This invention further provides an antibody which preferentially binds to an epitope present only on nicked human chorionic gonadotropin. In one embodiment, the antibody is a monoclonal antibody. The monoclonal antibody may be the monoclonal antibody designated B151 or B152.

This invention further provides a hybridoma cell line capable of producing a monoclonal antibody which preferentially binds to an epitope present only on nicked human chorionic gonadotropin. The hybridoma cell line may be the hybridoma cell line producing the monoclonal antibody designated B151 or B152.

The hybridoma cell-lines B152 and B207 were deposited pursuant to and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Feb. 3, 1998 and Apr. 4, 2000, respectively, under the following Designation Nos.: ATCC Designation No. HB-12467 (B152); and ATCC Designation No. PTA-1626 (B207).

This invention further provides a method for detecting the presence of human malignant cells in a sample of tumor cells, which comprises contacting the sample with an antibody directed to an epitope present on (i) the β subunit of human luteinizing hormone, (ii) the β subunit of human chorionic gonadotropin, (iii) intact human luteinizing hormone, or (iv) intact human chorionic gonadotropin, under conditions such that the antibody forms a complex with cells present in the sample if the epitope is present on the surface of the cells, and determining whether the antibody forms such a complex so as to thereby detect the presence of human malignant cells in the sample.

In one embodiment, the antibody is a monoclonal antibody. In the preferred embodiment, the monoclonal antibody is the monoclonal antibody designated B405, B406, B407, B408, B409, B412, B413, CTP101, CTP102, CTP103, CTP104 and CTP105.

As used herein, "malignant" means capable of metastasizing. As used herein, "tumor cells" are cells which originate from a tumor, i.e., from a new growth of different or abnormal tissue. The tumor cells may exist as part of the tumor mass, or may exist as free-floating cells detached from the tumor mass from which they originate.

As used in the subject invention, malignant cells include, but are in no way limited to, melanocarcinoma cells, nasopharyngeal carcinoma cells, lung non-small cell carcinoma cells, lung small cell carcinoma cells, breast cancer cells, urinary bladder carcinoma cells, uterine cervix squamous cell carcinoma cells, endometrial carcinoma cells, colonic carcinoma cells, prostate carcinoma cells, osteocarcinoma cells, rhabdomyosarcoma cells, leukemia cells, lymphoma cells, retinoblastoma cells and choriocarcinoma cells.

Determining whether the antibody forms such a complex may be accomplished according to methods well known to those skilled in the art. In the preferred embodiment, the determining is accomplished according to flow cytometry methods.

This invention further provides a method for determining whether a tumor present in a human subject is malignant which comprises obtaining a sample of cells from the tumor and detecting the presence of malignant cells in the sample according to the method of the subject invention so as to thereby determine whether the tumor is malignant.

Obtaining a sample of tumor cells may be accomplished using methods well known to those skilled in the art.

This invention further provides a method for obtaining an enriched population of live human malignant cells which comprises contacting a population of cells comprising live human malignant cells with an antibody directed to an epitope present on (i) the β subunit of human luteinizing hormone, (ii) the β subunit of human chorionic gonadotropin, (iii) intact human luteinizing hormone, or (iv) intact human chorionic gonadotropin, under conditions such that the antibody forms a complex with the cells present in the population if the epitope is present on the surface of the cells, and isolating the cells which form a complex with the antibody so as to obtain an enriched population of live human malignant cells.

In one embodiment, the antibody is a monoclonal antibody. In the preferred embodiment, the monoclonal antibody is the monoclonal antibody designated B405, B406, B407, B408, B409, B412, B413, CTP101, CTP102, CTP103, CTP104 and CTP105.

As used herein, an "enriched population of live human malignant cells" is a population of cells, wherein the percentage of cells being live human malignant cells is greater than the percentage of cells being live human malignant cells in the population of cells contacted with the antibody. For example, assume 10% of cell population A are live human malignant cells. Cell population A is contacted with an antibody directed to an epitope present on the β subunit of human luteinizing hormone or on intact human luteinizing hormone according to the method of the subject invention. Cells forming a complex with the antibody are isolated, and the isolated cells form cell population B. If greater than 10% of cell population B are live human malignant cells, then cell population B is an "enriched population of live human malignant cells."

The antibody may be bound to an insoluble matrix such as that used in affinity chromatography. As used in the subject invention, isolating the cells which form a complex with the immobilized monoclonal antibody may be achieved by standard methods well known to those skilled in the art. For example, isolating may comprise affinity chromatography using immobilized antibody.

Alternatively, the antibody may be a free antibody. In this case, isolating may comprise cell sorting using free, labeled primary or secondary antibodies. Such cell sorting methods are standard and are well known to those skilled in the art.

This invention further provides a method for determining the amount of intact luteinizing hormone in a sample which comprises contacting the sample with a suitable amount of antibody directed to an epitope present only on intact luteinizing hormone under conditions permitting the formation of a complex between the antibody and the epitope, determining the amount of complex so formed, and comparing the amount of complex so formed to a known standard so as to thereby determine the amount of intact luteinizing hormone in the sample.

In one embodiment, the antibody is a monoclonal antibody. In the preferred embodiment, the monoclonal antibody is the monoclonal antibody designated B413.

In another embodiment, the intact luteinizing hormone is intact human luteinizing hormone.

This invention further provides a method for determining the ovulatory stage of a subject which comprises obtaining a suitable sample from the subject, determining the amount of intact luteinizing hormone in the sample according to the method of the subject invention, and comparing the amount of intact luteinizing hormone so determined to a known standard so as to determine the ovulatory stage of the subject.

This invention further provides a method for determining the amount of intact follicle stimulating hormone in a sample which comprises contacting the sample with a suitable amount of antibody directed to an epitope present on intact follicle stimulating hormone under conditions permitting the formation of a complex between the antibody and the epitope, determining the amount of complex so formed, and comparing the amount of complex so formed to a known standard so as to thereby determine the amount of intact follicle stimulating hormone in the sample.

In one embodiment, the antibody is a monoclonal antibody. the preferred embodiment, the monoclonal antibody is the monoclonal antibody designated FSH-101.

This invention further provides a method for determining the ovulatory stage of a subject which comprises obtaining a suitable sample from the subject, determining the amount of intact follicle stimulating hormone in-the sample according to the method of the subject invention, and comparing the amount of intact follicle stimulating hormone so determined to the amount of intact follicle stimulating hormone present in a sample from a subject at a known ovulatory stage so as to determine the ovulatory stage of the subject.

This invention further provides a method for determining the amount of intact human chorionic gonadotropin in a sample which comprises contacting the sample with a suitable amount of antibody directed to an epitope present only on intact human chorionic gonadotropin under conditions permitting the formation of a complex between the antibody and the epitope, determining the amount of complex so formed, and comparing the amount of complex so formed to a known standard so as to thereby determine the amount of intact human chorionic gonadotropin in the sample.

In one embodiment, the antibody is a monoclonal antibody. In the preferred embodiment, the monoclonal antibody is the monoclonal antibody designated B151 or B152.

This invention further provides a method for determining whether a subject is pregnant which comprises obtaining a suitable sample from the subject, determining the amount of intact human chorionic gonadotropin in the sample according to the method of the subject invention, and comparing the amount of intact human chorionic gonadotropin so determined to a known standard so as to determine whether the subject is pregnant.

This invention further provides a method for determining the ovulatory stage of a subject which comprises obtaining a suitable sample from the subject, determining the amount of intact human chorionic gonadotropin in the sample according to the method of the subject invention, and comparing the amount of intact human chorionic gonadotropin so determined to the amount of intact human chorionic gonadotropin present in a sample from a subject at a known ovulatory stage so as to determine the ovulatory stage of the subject.

This invention further provides a method for determining the amount of free α subunit of human luteinizing hormone in a sample which comprises contacting the sample with a suitable amount of antibody directed to an epitope present on the a subunit of human luteinizing hormone under conditions permitting the formation of a complex between the antibody and the epitope, determining the amount of complex so formed, and comparing the amount of complex so formed to a known standard so as to thereby determine the amount of free a subunit of human luteinizing hormone in the sample.

In one embodiment, the antibody is a monoclonal antibody. In the preferred embodiment, the monoclonal antibody is the monoclonal antibody designated A501, A502, A201 or A202.

This invention further provides a method for determining whether a subject has a malignant tumor which comprises obtaining a suitable sample from the subject, determining the amount of free α subunit of human luteinizing hormone in the sample according to the method of the subject invention, and comparing the amount of free α subunit of human luteinizing hormone so determined to a known standard so as to determine whether the subject has a malignant tumor.

This invention further provides a method for determining the amount of nicked human chorionic gonadotropin in a. sample which comprises contacting the sample with a suitable amount of antibody which preferentially binds to an epitope present only on nicked human chorionic gonadotropin under conditions permitting the formation of a complex between the antibody and the epitope, determining the amount of complex so formed, and comparing the amount of complex so formed to a known standard so as to thereby determine the amount of nicked human chorionic gonadotropin in the sample.

In one embodiment, the antibody is a monoclonal antibody. In the preferred embodiment, the monoclonal antibody is the monoclonal antibody designated B151 or B152.

This invention further provides a method for determining whether a subject is pregnant which comprises obtaining a suitable sample from the subject, determining the amount of nicked human chorionic gonadotropin in the sample according to the method of the subject invention, and comparing the amount of nicked human chorionic gonadotropin so determined to an amount of nicked human chorionic gonadotropin correlative with a known state of pregnancy so as to determine whether the subject is pregnant. In the preferred embodiment, the suitable sample is a urine sample.

This invention further provides a method for determining whether a subject has a malignant tumor which comprises obtaining a suitable sample from the subject, determining the amount of nicked human chorionic gonadotropin in the sample according to the method of the subject invention, and comparing the amount of nicked human chorionic gonadotropin so determined to a known standard so as to determine whether the subject has a malignant tumor. In the preferred embodiment, the suitable sample is a urine sample.

This invention further provides a method for determining the likelihood of a fetus's being afflicted with Down's syndrome which comprises obtaining a suitable sample from the mother of the fetus, determining the ratio of the amount of free human chorionic gonadotropin β subunit in the sample to the amount of intact human chorionic gonadotropin in the sample, and comparing the ratio so determined to a known standard so as to determine the likelihood of the fetus's being afflicted with Down's syndrome.

Finally, the subject invention provides methods of detecting or quantitatively determining a hormone selected from the group consisting of human luteinizing hormone, human chorionic gonadotropin, or follicle stimulating hormone in a sample which comprise the steps of (a) contacting the sample with an immobilized first antibody directed to a first epitope present on the hormone under conditions permitting the formation of a complex between the immobilized first antibody and the hormone present in the sample; (b) removing the resulting first immobilized complex from the sample; (c) contacting the resulting first immobilized complex with a free, detectible second antibody directed to a second epitope present on the hormone under conditions permitting the formation of a complex between the first immobilized complex and detectible second antibody, with the proviso that the first and second antibodies are capable of simultaneously binding to the hormone; and (d) detecting or quantitatively determining the resulting complex between the first immobilized complex and detectable second antibody, so as to thereby detect or quantitatively determine the hormone present in the sample.

This invention will be better understood by reference to the Experimental Details which follow, but those skilled in the art will readily appreciate that the specific experiments detailed are only illustrative of the invention as described more fully in the claims which follow thereafter.

Experimental Details

I. The Development of a Panel of Monoclonal Antibodies to Human Luteinizing Hormone and its Application to Immunological Mapping and Two-site Assays Abstract Measurement of human luteinizing hormone in urine may be used to monitor the ovulatory cycle and is especially useful for large scale epidemiological studies because of the ease of sample collection. Because urinary LH, unlike serum LH, exists in a variety of forms including the intact hormone, subunits and fragments, urinary measurement is complex. It is difficult to make immunologic measurements useful for clinical assessments especially since it is unknown which of the LH forms are most useful in measuring urine. In order to develop means of measurement of hLH, its fragments and subunits in urine, an extensive library of monoclonal antibodies to hLH has been established to enhance the variety of forms of hLH which can be measured in biological fluids. Although the antibodies were produced by immunization with intact hLH, they were selected to exhibit sufficient diversity, multiple binding capabilities and high affinities to permit such wide-ranging measurements. This map indicates the presence of at least seven different epitopes on the surface of hLH. Three sites are in common with hCG.

Introduction

Sensitive and specific measurements of the gonadotropins are important for assessment and treatment of fertility problems (France, 1982). Treatment of infertility, in particular, is often dependent on accurate measurements of the time of ovulation by measurement of the hLH surge or urine (France, 1982; Singh et al., 1984; Lichtenberg et al., 1982; Kerin et al., 1990; Umapathysivam 1985). While such work has been directed towards improving assays for hCG (Vaitukaitis et al., 1972; Armstrong et al, 1984; Akar, et al. 1988, Krichevsky, et al. 1988; O'Connor et al., 1988), especially in efforts to measure the hormone in the presence of high concentrations of hLH, less effort has been devoted towards measuring hLH and its fragments in urine. Although hLH is usually measured in blood, urine is the fluid of choice for large scale epidemiological studies requiring gonadotropin measurements (Canfield et al., 1987). Several groups have published reports on the development of monoclonal antibodies to hLH, including some topological mapping studies (Soos & Siddle, 1983; Hunter et al., 1984; Chow et al., 1985; Odell & Griffin, 1987; Alonso-Whipple et al. 1988). Few specific monoclonal antibody assays have been used to measure hLH in urine. Such measurements are difficult to evaluate due to the presence of high levels of hLH fragments, its a and β subunit s (Ward et al., 1989). The precise structures and relative quantities of the various forms of hLH-derived molecules in urine is unknown; they are likely to vary with the precise time period of the ovulatory cycle. Some investigators have reported that particular hLH monoclonal antibodies fail to measure certain variants of hLH (Petterson et al, 1991; 1992). This high specificity of the monoclonal antibodies may occasionally limit their clinical utility. Such findings provide additional impetus for developing monoclonal antibodies that bind to different regions of the hormone's surface. Commercial two-site monoclonal assays, specific for heterodimeric hLH, were especially sensitive to low amounts of hLH variants in blood (Petterson et al,, 1991). Sensitive and specific measuring systems for hLH would require a multi-site immunoassay, i.e. IRMA (immunoradiometric assay), format of capture and detection of antibody pairs. This type of assay system is the most sensitive because it contains an excess of capture antibody that concentrates the ligand from a solution. If necessary, larger volumes of a solution could be used, therefore solutions of lower molarities could be measured than would normally be possible in a liquid phase type system. Efforts were directed to select antibodies which bound simultaneously to different portions of the molecule. The extensive library of hCG antibodies helped make these selections. The purposes for developing this library of antibodies were (1) to develop a greater variety of antibodies in order to improve the likelihood of identifying combinations of antibodies capable of measuring many forms of LH in biological fluids (2) to develop a library sufficient in the number of different antibodies to improve detection of unique variants of LH in biological fluids (3) to further expand immunological mapping of LH, and (4) to develop immunological tools for extraction and structural determination of the forms of hLH in urine.

Materials and Methods

Preparation of Immunogens, Immunization Methods and Selection of Animals

Intact hLH (NPA Lot no. AFP827013) was used for immunization at a dose of 30 µg of hLH per mouse. The hormone was diluted in saline and emulsified 1:1 with complete Freund's adjuvant (Calbiochem, San Diego, Calif.). hCGα subunit was conjugated to bovine thyroglobulin as described previously (Krichevsky et al., 1988) and used for immunization of mice at a dose of 5 µg of hCGα subunit, in conjugated form, per mouse. This immunogen was also diluted in saline and mixed 1:1 with complete Freund's adjuvant. Initial immunization and subsequent boosts were done by intraperitoneal (IP) injections. The mice were boosted twice with the same dose of immunogen at 4–5 week intervals. Nine days after the last booster injection, mice were bled and serum antibody levels to hLH and hCGα were determined by liquid phase double antibody RIA (Ehrlich et al., 1985; Krichevsky et al., 1988). Mice were boosted at 8 week intervals for another 8 months. The spleen from one mouse immunized with hLH and the spleen from a different mouse immunized with the hCGα subunit were each separately used for two fusions designated the 'hLH fusion' and the 'hCGα fusion' respectively.

Fusion and Selection of Cell Lines for Cloning

The mice used for both hLH fusions were given booster injections intravenously with 75 µg of intact hLH 72 h before fusion. The mouse used for the 'hCGα fusion' was boosted with 20 µg of hCGα conjugate in the same manner. A detailed protocol for production of hybridoma cell lines has been reported earlier (Krichevsky, et al., 1988) and it was used without modifications. Approximately 90% of the wells seeded with fusion products exhibited cell growth. Supernates from these wells were assayed by RIA (Ehrlich et al., 1985; Krichevsky et al., 1988) for the presence of antibodies against hLH, hLHβ, hCG, and hCGα in the 'hLH fusion' and for hCGα and hCG antibodies from the 'hCGα fusion'. In addition to the RIA screening, supernates from the hCGα fusion were tested for the ability to bind simultaneously with the previously reported A109 antibody to free α subunit as described (Ehrlich et al., 1985). Cells growing in wells whose supernates bound selected tracers were propagated until they reached a density of $3 \times 10^7$ to $5 \times 10^7$. At this time, cells were frozen in liquid nitrogen and the supernates saved for further testing. Supernates were tested for antibodies which could bind highly purified preparation of hLH, hLHβ, hCG and hCGα both in liquid phase RIA and in solid phase 'cooperative' RIAs either simultaneously with already existing antibodies or at the same time with each other. (Ehrlich et al., 1982, 1985; Krichevsky et al. 1988). Cloning of selected cells was performed by the limiting dilution method with enough subclonings to insure monoclonality (Coller & Coller, 1983). Antibody affinities were determined by the method of Scatchard (1949).

One antibody (B207) used in IRMA assays was cloned from a fusion reported previously (Krichevsky et al., 1988).

IRMA for Intact hLH

Construction of immunoradiometric assays (IRMAs) and characterization of their specificity and sensitivity was described previously (O'Connor et al., 1988). briefly, microtiter wells (Immun II, Dynatech Laboratories Inc.) were coated with 200 µl of a 12 µg/ml solution of B406 (this report) in 0.2 M carbonate buffer pH 9.5. After overnight incubation at 4° C. the coating antibody solution was aspirated, the wells washed (4×) with wash solution (0.15 M NaCl+0.05% Tween-20) and clocked with a 1% bovine serum albumin solution (with 0.1% $NaN_3$) for 3 h at room temperature or overnight at 4° C. The BSA solution was aspirated and 200 µl of hLH standard, covering a range of 0.098–50 ng/ml hLH, and controls in assay buffer (0.01M $NaHPO_4$, 0.15 M NaCl, 0.01 M EDTA, 0.1% $NaN_3$, 0.1% bovine gamma globulin, pH 7.4) were added in duplicate to the wells. Urine samples were thawed, pH adjusted (1.0 M Tris pH 9.0, 50 µl/ml of urine), centrifuged and added to the wells. The plates were covered with a plate sealer and incubated overnight at room temperature. The wells were then aspirated, washed (6×) with wash solution and approximately 100000 c.p.m. of radiolabeled A201 (this report) in 200 µl of buffer was added to each well. Incubation was again carried out overnight at room temperature. The tracer solution was aspirated and the wells washed (6×) with wash solution. The wells were placed in glass 12×75 mm tubes and counted in a gamma counter. Doses were interpolated from a smoothed spline fit of the count data. The least detectable dose was defined as +3SD from multiple replicates of the NSB tubes.

The assay for hLH free β subunit was essentially identical with the exception of the identities of the antibodies employed.

Steroid Glucuronide Enzyme Immunoassay

The assay for pregnanediol-3-glucuronide was performed with reagents which included polyclonal antibodies, raised in rabbits and a detection system consisted of the steroid glucuronide, conjugated to horseradish peroxidase. The substrate for color development was ABTS (2.2'-Azinobis (3-ethylebenz-thiazolinesufonic acid)) (Kirkegaard and Perry, Gaithersburg, Md.).

Briefly, microtiter wells (Corning Easy Wash, Corning, N.Y.) were coated (50 μl well) with a solution of antibody in coating buffer (sodium carbonate 0.05 M. pH 9.6) overnight at 4° C. The wells were then washed (5×) with wash solution (0.15 M NaCl, 0.05% Tween-20). After that 50 μl of EIA buffer (0.1 mM PBS, 0.1% BSA, pH 7.0) were added into each well and plates were allowed to stand at room temperature for 2 h. Following the preincubation, 20 μl of either a urine sample to be tested (1:100 dilution) or an appropriate standard was placed into each well, along with 50 μl of RIA buffer and 50 μl of the appropriate steroid glucuronide HRP conjugate (total volume 120 μl/well). The wells were then incubated either for 2 h at room temperature or overnight at 4° C. After this incubation the plates were again washed (5×) with the wash solution (same as above) and then 100 μl of substrate solution (40 mM ABTS in 0.05M citrate buffer, pH 4.0) were placed into each well. Plates were then gently shaken until color developed (approximately 1 h). A stop solution (ABTS Peroxidase Stop Solution, Kirkegaard and Perry, Gaithersburg, Md.) was added (100 μl/well), and plates read at 405 nm (UVMAX, Molecular Devices, Menlo Park, Calif.). The plate absorbance data was reduced by employing a polynomial curve fit.

Results

1. Selection and Characteristics of Antibodies to hLH

The library of antibodies to hLH was selected by identifying the cells from each antibody-producing fusion which reacted uniquely to hLH, and also screening for pairs of antibodies capable of binding to hLH simultaneously. Some of the antibodies were developed earlier than hCG which has close structural homology to hLH (Krichevsky et al., 1988).

hLH-immunized mouse spleen cells were grown in 96 well tissue culture plates and the supernates were screened for specific binding properties to radiolabeled hLH, hLHβ, hCG and hCGα. Initially, 61 wells reacted positively with at least one of the tracers. Ten of these wells subsequently lost binding activity; this occurrence represents an attrition rate of 16%. All well supernates which bound radiolabeled tracers at levels of 3–5 times of background were considered positive. The majority of remaining supernates contained antibodies binding to radiolabeled intact hLH immunogen exclusively (42%) (see Table 1). A significant proportion (22%) of the wells contained cells producing antibodies to both intact hLH and its β subunit, only 15% bound to the α subunit and 7% bound strictly to the β subunit. Antibodies directed solely to the free subunits were unexpected since hLH immunogen appeared to be intact (i.e. there were no free subunits, fragments or peptide-bond cleavages) as determined by gel electrophoresis and amino acid sequence analysis (data not shown). Two wells produced antibodies which bound all of the tracers; one recognized intact hLH, hCG, and α subunit; the other recognized intact hLH and α subunit. These results indicated that an extensive panel of antibodies to intact hLH, as well as to its subunits, could be obtained by immunization with this preparation of intact hLH.

TABLE I

| Tracer | Number of Positive Wells | % of Total Antibody Producing Wells |
| --- | --- | --- |
| hLH | 25 | 41.7 |
| hLHβ | 4 | 6.6 |
| hLH/hLHβ | 13 | 21.7 |
| hLH/hCG | 5 | 8.3 |
| hLH, hLHβ hCG, hCGα | 2 | 3.3 |
| hLH, hCG, hCGα | 1 | 1.7 |
| hLH/hCGα | 1 | 1.7 |
| hCGα | 9 | 15.0 |
| Total | 60 | 100% |

The cloned antibodies were grouped together based on their capabilities to bind two different sites on the hormone simultaneously and on their binding patterns to labeled tracers in liquid and solid phase systems (Table 2). The nomenclature of these binding sites is consistent with the format developed by previously reported antibodies to hCG (Krichevsky et al., 1988), based on simultaneous binding of pairs of antibodies or mutual inhibition in liquid and solid phase assays. For example, antibodies directed to the same site will bind to the hormone or subunits simultaneously, while those directed to different sites will inhibit at the same time. Using the simultaneous binding and inhibition of binding criteria, the reported antibodies have been mapped to seven different epitopes on hLH (see FIG. 1). Some of these binding sites are shared with hCG while other are unique to hLH. Table 2 which details the characteristics of the newly developed antibodies includes binding studies with antibodies developed earlier to hCG as described in Krichevsky, et al, (1988). These antibodies were B120, B203 and B206 which were developed to hCGβ core fragment. Antibody B120 binds to the hCGβ core fragment and both hLHβ and hCGβ subunits with affinities of $1 \times 10^{10}$ L/M. This antibody binds to the heterodimeric hormones with a much lower affinity of $10^7$ L/M. Antibodies B203 and B206, developed to the same hCGβ core fragment immunogen, bind hCG, hLH and their subunits with affinities of $10^{10}$ to $10^{11}$ L/M. Both have higher affinities toward hCG-derived molecules. A105 was developed from hCGα and binds both hCG and hLH, as well as both of their α subunits, with an affinity of $3 \times 10^9$ L/M.

Table 2 starts with site 11 antibodies since the site 1 type is associated with the unique β subunit COOH-terminal epitope on hCG and is not present on hLH. The characteristics of each of these new antibodies to hLH appear in table 2. Also included in Table 2 are the characteristics of antibody B207 developed to the hCGβ fragment. This antibody binds to hLH and the hLHβ subunit and was used to construct the IRMA systems described in this paper. The affinities for each of these antibodies to hCG and hLH as well as their subunits appear in Table 3.

Four antibodies to site II, which is present on both hLH and hCG, are listed in Tables 2 and 3. Two were developed from mice immunized with hLH (B411 and B412) and two (B203 and B206) were from mice immunized with the hCGβ fragment (Krichevsky, et al. 1988) as described above. All four display the same specificity profile: each binds to intact hLH, hCG, hCGβ and hLHβ as well as to the hCGβ fragment, but not to the α subunit; none of these antibodies bind to labeled FSH. Two antibodies were developed from mice immunized with hLH (B411 and dB412) and both have similar affinities to hCG and hLH, in the range of $10^9$ to $10^{10}$ L/M (Table 3). Herein, B412 is the only antibody of the IgA subclass. This unusual subclass is especially useful for mapping hLH since the antibody-hormone complex can be precipitated by anti-IgA antisera.

TABLE 11

| BINDING SITE ON EPITOPE MAP | ANTIBODY (ISOTYPE) | ANTIBODY BINDS TO THE FOLLOWING ANTIGENS IN LIQUID PHASE R1A | | | | | ANTIBODY BINDS SIMULTANEOUSLY WITH ANTIBODIES IN SOLID PHASE ASSAY | ANTIBODY CANNOT BIND SIMULTANEOUSLY WITH ANTIBODIES IN SOLID PHASE ASSAY |
|---|---|---|---|---|---|---|---|---|
| | | hLH | hCG | hLHβ | hCGβ | hCGα | | |
| KB22 II | B-411 (IgG1) | 100% | 60% | 120% | 60% | ND | B201, A105, B207, A501, B409 | B203, B206 |
| KB23 II | B412 (IgGA) | 100% | 80% | 300% | 200% | ND | A105, A201, A202, A501, A502 | B203, B206, B207 |
| II | B207 (IgG1) | 100% | NT | 1000% | NT | ND | A105, A201, A202, B408, A501, A502, B201, A407, B405, B406, B411, B409 | B203, B206 |
| KB11 III | B405 (IgG2s) | 100% | ND | ND | ND | ND | A105, A201, A202, B203, B206, B207, B411 | B406, A501, A502, B201 |
| KB12 III | B406 (IgG2a) | 100% | ND | ND | ND | ND | A105, A201, A202, B203, B206, B207, B411 | B405, A501, A502, B201, |
| IIIa | A501 (IgG1) | 3% | 0.7 | ND | ND | 100% | A105, A201, A202, B203, B206, B207, B411 | B409, B405, B201, B406, A502, B408 |
| IIIa | A502 (IgG1) | 0.1% | .2% | ND | ND | 100% | A105, A201, A202, B203, B206, B207, B411 | B409, B405, B203, B406, A501, B409 |
| V | A201 (IgG1) | NT | 7.5% | ND | NT | 100% | B203, B206, B207, A501, A502, A407, B411 | A105, A202, B409, |
| V | A202 (IgG1) | NT | 40% | ND | NT | 100% | B206, B207, B405, B406, A501, A502, A201 | A105, A201, B409 |
| KB31 VI | B408 (IgG1) | 100% | ND | 830% | ND | ND | B203, B206, B207, B209, A407 B409 | B405, B406, A501, A502, B201, A105 |
| KB21 VII | B409 (IgG1) | ND | ND | 100% | ND | ND | B203, B206, B207, B408, B201, B411, A105, A201 | B405, B406, A501, A502, |
| KB13 VIII | A407 (IgG1) | 100% | 100% | ND | ND | ND | B203, B206, B207, B405, B406, A501, A502, A105, A201, A202 | B409, B411 |

NT = NOT TESTED
ND = NONE DETECTABLE

Site III antibodies fall into two types. This is indicated by designating the types as III and IIIa on Table 2. Two antibodies, B405 and B406, bind only to hLH in both liquid and solid phase systems (Table 2) with affinities of $8 \times 10^7$ to $8 \times 10^8$ L/M respectively (Table 3) and are designated as site III types. Two other antibodies (A501 and A502), listed as site IIIa antibodies, bind weakly to intact hLH but strongly to free α subunit (Table 3). Although they cannot bind simultaneously with other class III antibodies, they do bind simultaneously with region V antibodies to the α subunit. They are obviously directed to a close but distinct region of the hormone and are thus designated as belonging to site IIIa.

One antibody developed earlier to a fragment of the hCGβ subunit, B201 (Krichevsky et al., 1988), is listed as class IV and binds only to the β subunit s of hLH and hCG with an affinity of $10^{10}$ L/M. This is the first reported case of a hLH free β subunit antibody that can discriminate between subunits and intact heterodimers.

TABLE III

| Antibody | Tracer | hLH | hCG | Competitors hLHβ | hCGβ | hCGα |
|---|---|---|---|---|---|---|
| B411 | hLH | $5 \times 10^9$ | $3 \times 10^9$ | $3 \times 10^9$ | $2 \times 10^9$ | ND |
| | hLHβ | $3 \times 10$ | $3 \times 10^9$ | $6 \times 10^8$ | $3 \times 10^9$ | ND |
| | hCG | NT | $3 \times 10^9$ | NT | $1 \times 10^9$ | ND |
| | hCGβ | NT | NT | NT | $3 \times 10^9$ | ND |
| B412 | hLH | $1 \times 10^{10}$ | NT | $3 \times 10^{10}$ | NT | NT |
| | hLHβ | $2 \times 10^{10}$ | NT | $3 \times 10^{10}$ | NT | NT |
| | hCG | $2 \times 10^{10}$ | $8 \times 10^9$ | $1 \times 10^{10}$ | $2 \times 10^{10}$ | NT |
| | hCGβ | $3 \times 10^9$ | $7 \times 10^9$ | $6 \times 10^9$ | $6 \times 10^9$ | NT |
| B405 | hLH | $8 \times 10^7$ | ND | ND | ND | ND |
| B406 | hLH | $8 \times 10^8$ | ND | ND | ND | ND |
| A501 | hCG | NT | $4 \times 10^7$ | ND | ND | NT |
| | hLH | $2 \times 10^8$ | NT | NT | NT | NT |
| | hCGα | NT | $3 \times 10^7$ | ND | ND | $6 \times 10^9$ |

TABLE III-continued

| Antibody | Tracer | hLH | hCG | Competitors hLHβ | hCGβ | hCGα |
|---|---|---|---|---|---|---|
| A502 | hCG | ND | ND | ND | ND | ND |
| | hLH | $5 \times 10^8$ | NT | ND | ND | NT |
| | hCGα | NT | $1 \times 10^7$ | ND | ND | $5 \times 10^9$ |
| A201 | hCGα | NT | $3 \times 10^7$ | ND | NT | $4 \times 10^9$ |
| A202 | hCGα | NT | $4 \times 10^7$ | ND | NT | $1 \times 10^9$ |
| B408 | hLH | $7 \times 10^8$ | ND | $2 \times 10^{10}$ | ND | ND |
| | hLHβ | NT | ND | $6 \times 10^{10}$ | ND | ND |
| B409 | hLH | ND | ND | ND | ND | NT |
| | hLHβ | ND | ND | $3 \times 10^9$ | ND | NT |
| | hCG | ND | ND | ND | ND | NT |
| | hCGβ | ND | ND | ND | ND | NT |
| A407 | hLH | $2 \times 10^8$ | NT | NT | NT | ND |
| | hCG | NT | $2 \times 10^8$ | NT | NT | ND |

ND - Non-detectable
NT - Not tested

There are three site V antibodies listed which bind both intact hLH and its free α subunit. One antibody, developed to intact hCG, A105, was reported earlier (Krichevsky et al. 1988). The other two antibodies, A201 and A202, were developed to the α subunit using hCGα as the immunogen. Antibodies from these cell lines bound better to radiolabeled hCGα subunit than to labeled intact hCG in liquid phase assays (Table 3). These two antibodies, A201 and A202, were selected for their ability to bind simultaneously with antibody A109 (a site III antibody) ((Norman et al., 1985) to α subunit (see Materials and Methods)). Antibodies A201 and A202 bound simultaneously with A109, A501 and A502 to free α subunit (Table 2). These new antibodies led to IRMA assays for intact hLH that were superior to those using the earlier developed antibody, A105 (see Table 4 and the text below).

Figure 1:
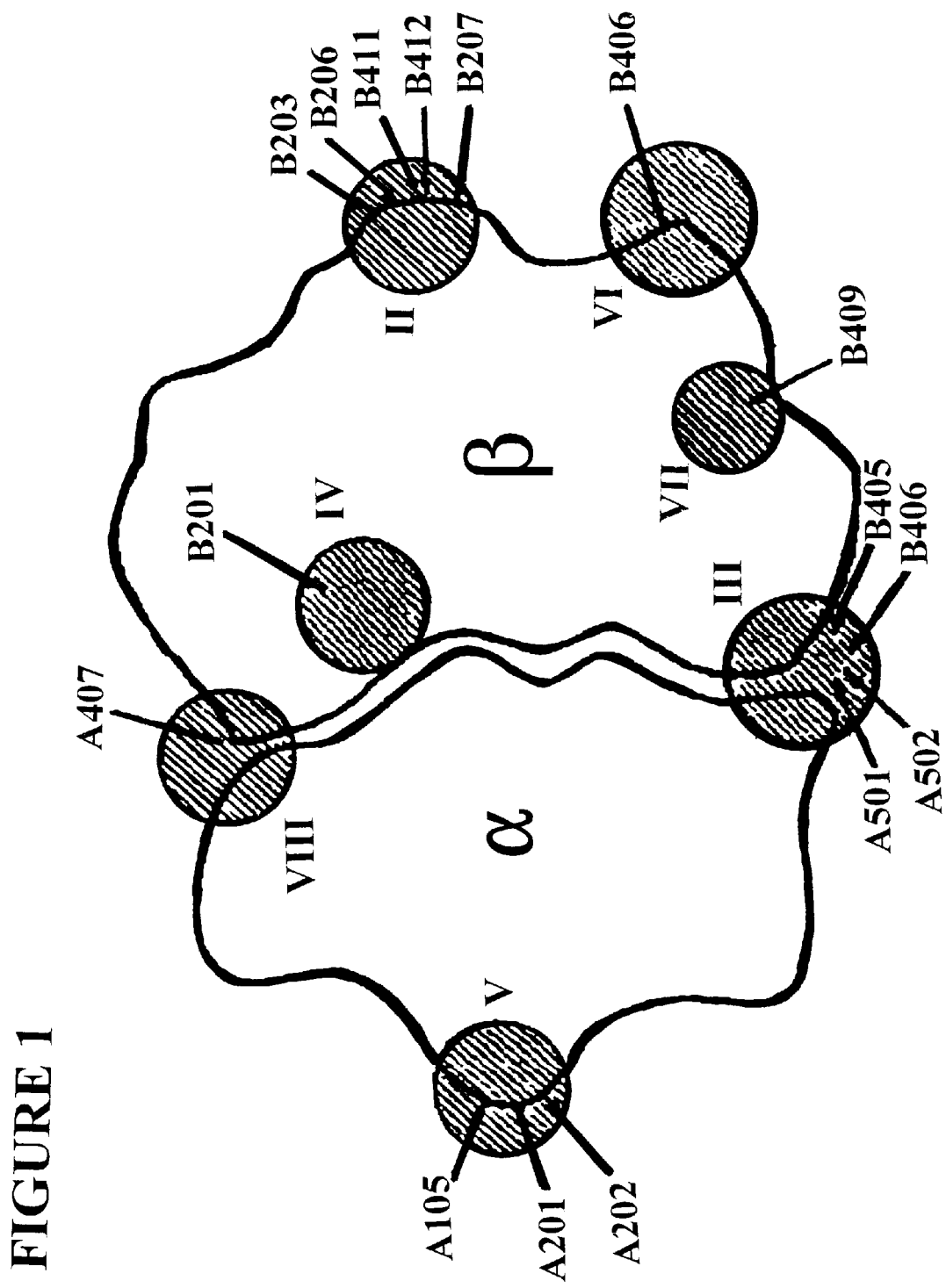
FIG. 1

Such antibody is assigned to separate binding sites VI, VII and VIII. These are: B408, which binds only to hLHβ in liquid phase RIA (Site VI); B409, which binds to hLH and its B subunit but not to hCG or hCGβ and is thus an hLH-specific type of antibody (Site VII); A407, which binds to intact hCG and hLH but to neither of their iodine-labeled free subunits in liquid phase assays (Site VIII). In solid phase assays, this antibody bound in a limited sense to free α subunit. Molecular biological studies indicated that this antibody reacted with residues of the α subunit exclusively. The latter antibody is of special interest since it selects for intact dimeric hCG or hLH from mixtures containing both intact hormones and their free subunits and fragments. A407 is the only antibody in this library which binds simultaneously with all of the other antibodies binding to intact hormone species, it was therefore assigned in a unique binding site, site VII (FIG. 1).

TABLE IV

Labeled Antibody sensitivities (minimal detectable doses) in pmoles/ml of IRMA systems

| Capture Antibody Concentration | Antigen | B203 | B206 | B207 | B411 | B405 | B406 | A501 | A502 | B201 | A105 | A201 | B409 | A407 |
|---|---|---|---|---|---|---|---|---|---|---|---|---|---|---|
| B203 (5 μg/well) | βhCG | — | a | a | a | a | a | a | a | 0.20 | a | NT | 0.20 | a |
| | hCG | — | 0.7 | a | a | a | a | 0.2 | 0.3 | a | 0.02 | NT | 1.70 | 0.02 |
| | hLH | — | 0.7 | a | a | 0.03 | 0.05 | 0.3 | 0.6 | a | 0.80 | NT | 0.20 | 0.0 |
| | βhLH | — | 1.5 | a | a | a | a | a | a | 1.5 | a | NT | 0.02 | a |
| B206 (5.8 μg/well) | βhCG | a | — | a | a | a | a | a | a | 0.10 | a | NT | 1.0 | a |
| | hCG | a | — | a | a | a | a | 0.4 | 0.30 | a | 0.03 | NT | 2.1 | 0.02 |
| | hLH | a | — | a | a | 0.03 | 0.05 | 0.3 | 0.50 | a | 0.30 | NT | 0.14 | 0.01 |
| | βhLH | a | — | a | a | 1.70 | a | a | a | 1.0 | a | NT | 0.03 | 2.0 |
| B207 (5.0 μg/well) | βhCG | a | a | — | NT | NT | NT | NT | NT | NT | NT | a | 0.28 | a |
| | hCG | a | a | — | NT | NT | NT | NT | NT | NT | NT | 0.02 | a | 0.02 |
| | hLH | a | a | — | NT | NT | NT | NT | NT | NT | NT | 0.05 | 0.05 | 0.02 |
| | βhLH | a | a | — | NT | NT | NT | NT | NT | NT | NT | a | 0.01 | a |
| B411 (2.6 μg/well) | βhCG | a | a | 0.3 | — | a | a | 0.60 | a | 0.01 | a | a | 0.30 | a |
| | hCG | a | a | a | — | a | a | 0.05 | 0.08 | 0.13 | 0.085 | 0.021 | a | 0.011 |
| | hLH | a | a | 0.06 | — | 0.01 | 0.006 | 0.07 | 0.21 | 0.35 | 0.208 | 0.013 | 0.10 | 0.006 |
| | βhLH | a | 1.4 | 0.06 | — | 0.69 | 0.347 | a | a | 0.05 | a | a | 0.01 | a |
| B405 (2.6 μg/well) | βhCG | a | a | a | a | — | a | a | a | a | a | a | a | a |
| | hCG | a | a | a | a | — | a | a | a | a | a | a | a | a |
| | hLH | 0.02 | 0.05 | 0.01 | a | — | a | a | a | a | 0.01 | 0.05 | a | 0.052 |
| | βhLH | 1.7 | 0.7 | 0.7 | a | — | a | a | a | a | a | a | a | a |
| B406 (5.0 μg/well) | βhCG | a | a | a | a | a | — | a | a | a | a | a | a | a |
| | hCG | a | a | a | a | a | — | a | a | a | a | a | a | a |
| | hLH | 0.02 | 0.05 | 0.01 | a | a | — | a | a | a | 0.208 | 0.007 | a | 0.052 |
| | βhLH | 1.4 | 1.4 | 0.5 | a | a | — | a | a | a | a | a | a | a |
| A501 (9 μg/well) | hCG | 0.6 | 0.2 | 0.1 | a | a | a | — | a | a | 0.05 | 0.011 | a | 1.36 |
| | hLH | 0.2 | 0.5 | 0.03 | a | a | a | — | a | a | 0.02 | 0.013 | a | 0.83 |
| | αhCG | a | a | a | a | a | a | — | a | a | 0.005 | 0.005 | a | a |
| A502 (9.4 μg/well) | hCG | 0.5 | 0.08 | 0.05 | a | a | a | a | — | a | 0.05 | 0.043 | a | 0.68 |
| | hLH | 0.1 | 0.1 | 0.02 | a | a | a | a | — | a | 0.03 | 0.026 | a | 0.83 |
| | αhCG | a | a | 2.5 | a | a | a | a | — | a | 0.02 | 0.005 | a | a |
| B201 (4 μg/well) | βhCG | 0.1 | 0.05 | 0.005 | 0.05 | a | a | a | 2.3 | — | a | NT | 0.25 | NT |
| | hCG | 2.0 | 0.4 | 0.09 | 0.45 | a | a | a | a | — | a | NT | 1.7 | NT |
| | hLH | 0.8 | 0.3 | 0.02 | 0.45 | a | a | a | a | — | a | NT | 0.1 | NT |
| | βhLH | 0.1 | 0.08 | 0.005 | 0.14 | a | a | a | a | — | a | NT | 0.02 | NT |
| A105 (5 μg/well) | hCG | 0.05 | 0.02 | 0.06 | 0.68 | a | a | 0.17 | a | a | — | NT | a | 0.085 |
| | hLH | 0.15 | 0.20 | 0.02 | 1.67 | 0.01 | 0.01 | 0.13 | 0.83 | a | — | NT | a | 0.013 |
| | αhCG | a | a | a | a | a | a | 0.001 | 0.02 | a | — | NT | a | a |
| A201 (5 μg/well) | hCG | 0.05 | 0.02 | 0.06 | a | a | a | 0.085 | 0.043 | NT | a | — | a | 0.043 |
| | hLH | 0.05 | 0.08 | 0.01 | a | 0.01 | 0.013 | 0.026 | 0.013 | NT | a | — | a | 0.013 |
| | αhCG | a | a | a | a | a | a | 0.003 | 0.003 | NT | a | — | a | 0.862 |
| A202 (10 μg/well) | hCG | NT | 0.02 | 0.04 | NT | a | a | 0.042 | 0.043 | NT | a | NT | a | NT |
| | hLH | NT | 0.06 | 0.01 | NT | 0.01 | 0.006 | 0.026 | 0.013 | NT | a | NT | a | NT |
| | αhCG | NT | 0.7 | a | NT | a | a | 0.003 | 0.003 | NT | a | NT | a | NT |
| B409 (15.6 μg/well) | βhCG | 0.06 | 0.02 | 0.5 | a | a | a | a | a | 0.2 | a | a | — | a |
| | hCG | 1.80 | a | a | a | a | a | a | a | 1.5 | a | a | — | a |
| | hLH | 0.10 | 0.1 | 0.1 | a | a | a | a | a | 1.7 | a | a | — | a |
| | βhLH | 0.02 | 0.04 | 0.01 | a | a | a | a | a | 0.08 | a | a | — | a |
| B408 (16 μg/well) | βhCG | a | a | a | a | a | a | a | a | a | a | a | a | a |
| | hCG | a | a2 | a | a | a | a | a | a | a | a | a | a | a |
| | hLH | 0.01 | 0.05 | 0.1 | a | a | a | a | a | a | a | 0.1 | 0.01 | 0.052 |
| | βhLH | 0.01 | 0.01 | 0.006 | a | a | a | a | a | a | a | a | 0.01 | a |
| A407 2.5 μg/well) | βhCG | a | a | a | a | a | a | a | a | a | a | a | a | — |
| | hCG | 0.13 | 0.16 | 0.06 | a | a | a | 0.25 | 0.67 | a | 0.085 | 0.043 | a | — |
| | hLH | 0.03 | 0.16 | 0.008 | a | 0.01 | 0.013 | 0.21 | 0.42 | a | 0.208 | 0.013 | a | — |
| | βhLH | a | a | 0.9 | a | a | 1.4 | a | a | a | a | a | a | — | a = Greater than 2.5 pmol/ml
NT = Not tested.
The position of antibody identity in the matrix is indicated by "—"

2. Assessment of Simultaneous Antibody Binding for Assay Development

Table 4 represents a summary of studies of the various possible IRMA systems, showing the minimal detectable concentrations of hormones or subunits which can be measured by various permutations of capture and detection antibodies. This table also indicates simultaneous binding as sell as competitive binding of the various antibodies. The data contained in this table are essential for meeting the goals of generating specific assays to measure hLH and its free β subunit as well as to produce an immunological map of hLH (FIG. 1). Each capture antibody was coated with Immulon-2 plates to extract antigens from the sample solution. Radiolabeled detection antibodies were used to measure the total antigen bound to the capture antibody. Only detection antibodies capable of binding to an accessible epitope on the captured antigen gave a signal. Two antibodies, B408 and A202, could not be used as detection antibodies since they lost binding capacities after radiolabeling.

The data shown in Table 4, along with data from earlier studies (Krichevsky et al., 1988) and the result of liquid phase assays (data not shown), were used to produce the epitope map of hLH (FIG. 1). Capture antibodies appeared along the left column while radiolabeled detection antibodies appeared across the top of Table 4. The types of assays which could be developed using antibodies from each of the assigned binding sites are as follows:

Antibodies to Site II

None of the site II antibodies exhibit sufficient specificity to be used to capture hLH or its β subunit from solution; this is because they bind to both intact hormones and subunits. They can be used in assays to measure total hCG/hLH-related immunoreactive materials in combination with either B201 or A407 as the detection antibody.

Antibodies to Site III

B405 and B406 are useful as capture antibodies to extract intact hLH from solutions. A201 and A407 may be used as the detection antibody to develop assays for intact hLH at sensitivities as low as 7 fmoles/ml. As described in the Materials and methods section, the minimal detectable dose was that quantity of ligand which produced a signal over three standard deviations from the non-specific response factor. Site IIIa antibodies (see tables 2,4) may be used to measure free α concentrations when used with antibodies to region V. For example, an assay composed of A105 (Site V) as capture antibody and A501 as the labeled tracer antibody results in an assay which will detect free α subunit at a sensitivity of 1 fmol/ml.

Antibodies to Site IV

B201 is the only antibody in this library that recognizes free β hLH and β fragment and not intact hormone. It is not useful as a capture antibody since it will extract both the β subunit and β fragments of hCG and hLH but it is a very useful detection antibody. For example, using B201 as a detection antibody and B409 as capture, hLHβ may be measured with a sensitivity of 80 fmol/ml.

Antibodies to Site V

From the data in Table 4, it is apparent that it would be useful to obtain more antibodies to subsets of this region because different antibodies could be developed from this general area which would have difference specificities and sensitivities. When used as capture to measure intact hLH, either A201 alone or A202, in conjunction with B406, produces a sensitivity of 7 fmoles/ml, in comparison with the earlier described A105, which has a sensitivity of only 208 fmoles/ml.

Antibodies to Site VI

B408 was discussed above; it is used in a specific assay for hLH and hLHβ subunit.

Antibodies to Site VII

B409 binds only to labeled hLHβ subunits in liquid phase RIA. When used as a detection antibody with B408 as the capture antibody, both intact hLH and β subunit can be measured with sensitivities of 3 fmoles/ml for hLH and 0.5 fmoles for β subunit.

Antibodies to Site VIII

A407 binds simultaneously with all other antibodies (except those that are β subunit-specific) listed in Table 4. A407 can be used together with antibodies B405, B406 and B408 for construction of specific hLH assays with sensitivities of 50 fmoles/ml.

4. Construction of Immunoradiometric Assays for Urinary hLH

From the matrix of monoclonal antibodies presented in Table 4, appropriate pairs were chosen for the development of urinary hLH assays. For measuring the intact hLH molecule, a combination consisting of an alpha-beta interface site III-directed immobilized capture monoclonal (B406) and an α subunit-directed detection antibody (A201) were employed. For the assay of hLH free β subunit , a site VII antibody (B409) was used for capture and a site VI (B408) for detection. The sensitivity and specificity characteristics of these assays are presented in Table 5.

TABLE V

| ANTIGEN | hLH | BhLH | B frag | BhCG | hCG | ALPHA |
|---|---|---|---|---|---|---|
| B409-B408 ASSAY FOR BhLH | | | | | | |
| % CROSS ACTIVITY | 10% | 100% | <1% | <1% | <1% | <1% |
| LOWEST DETECTABLE DOSE pmol/ml | 0.003 | 0.0005 | >2.4 | >45 | >27 | >13.8 |
| B406-A201 ASSAY FOR hLH | | | | | | |
| % CROSS ACTIVITY | 100% | 1% | <1% | <1% | <1% | <1% |
| LOWEST DETECTABLE DOSE pmol/ml | 0.01 | 1.5 | >2.4 | >45 | >27 | >13.8 |

Figure 2:
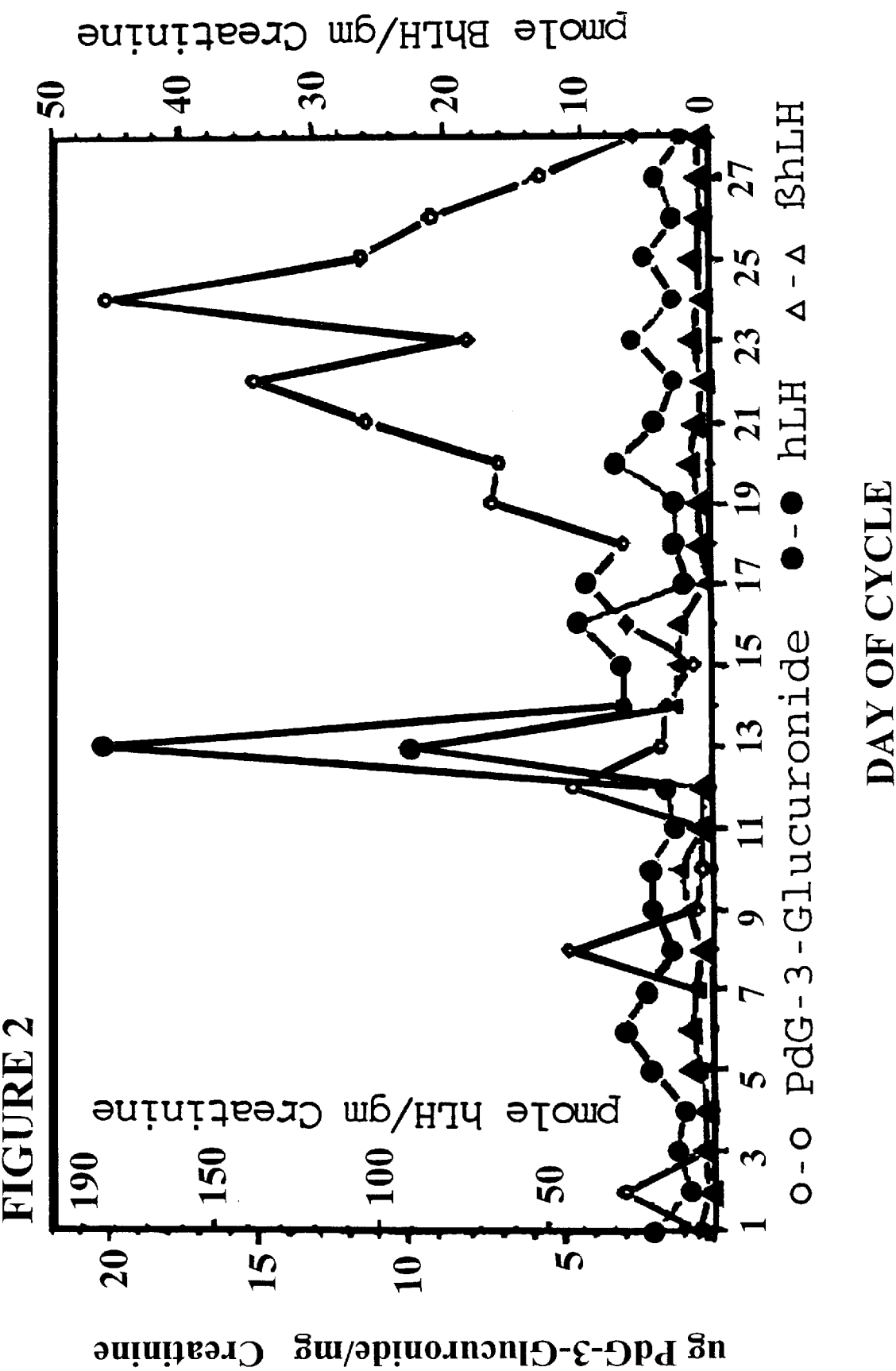

The practical application of these assays in the definition of a normal menstrual cycle by urinary measurements is illustrated in FIG. 2. Urine was collected daily from a normally cycling subject, and immediately frozen using glycerol as a cryoprotectant (Livesey et al., 1983). In addition to assays for intact hLH and free hLH β subunit , the urinary metabolite pregnanediol-3-glucuronide was assayed to document ovulation and the presence of the luteal phase. All values have been indexed to creatinine. The Figure illustrates a clear intact hLH preovulatory surge. A lesser peak of hLH free β subunit occurs concurrently. The increasing level of pregnanediol-3-glucuronide provides additional support for the detection of an ovulatory cycle.

Discussion

Measurement of the glycoprotein hormones has greatly benefitted from monoclonal antibody technology which has permitted accurate quantitation of one hormone or fragment with high sensitivity and good specificity, even in the presence of much larger quantities of immunologically-related materials. This enhancement was accomplished by combining the unique specificities of two monoclonal antibodies on two-site immunoassay (Soos et al., 1984; Chow et al., 1985; Norman et al., 1985; Schwarz et al., 1986; Odell & Griffin, 1987; Berger et al., 1988). The general approach used to develop these assays is to assess the specificity and affinity of each individual antibody to an analyte and then to compare individual antibody pairs. If two antibodies can bind to the analyte simultaneously, each antibody is designated as binding to a different site on the ligand. If two antibodies compete for binding to a ligand, they are designated as binding to the same or a closely neighboring site. This process of determining relative binding sites on a ligand, essentially steric-inhibition assays, has been termed 'immunological mapping'. Immunological mapping of these hormones has not only advanced measurement techniques but has also helped in understanding the topographical relationships among some major surface features. Human chorionic gonadotropin has been most extensively studies in this manner (Hussa, 1987). Such mapping has also been performed with other glycoprotein hormones, hLH (Soos & Siddle, 1983; Alonso-Whipple et al. 1988) hFSH (Berger et al., 1988), hTSH (Livesey et al., 1983) but to a lesser extent.

This strategy in developing antibodies to hLH involved the use of antibody selection techniques that emphasized development of antibodies which were capable of simultaneous binding. Such antibodies would allow both the epitope mapping of the hormone surface as well as the selection of antibody combination from which specific and sensitive clinical assays could be developed. Several other groups have developed (Soos & Siddle, 1983; Chow et al., 1985; Odell & Griffin, 1987) or characterized (Alonso & Whipple et al., 1988) antibodies to hLH. However, versatile immunoassay systems, which can measure hLH and its subunits and fragments with adequate sensitivity in a variety of biological fluids, were undeveloped prior to the subject invention. Most hLH assays were developed for serum measurements (Odell et al., 1967) and some were later adapted to detect hLH in urine (Umapathysivam & Jones, 1985; Kerin et al., 1990). It was desirable to develop assays chiefly for use in urine (for ease of sample collection), which would be especially useful in epidemiological studies (Wilcox, et al. 1988). Earlier, assays were developed to measure hCG and its subunits and fragments separately and specifically in urine in the midst of high concentrations of cross-reacting material. Luteinizing hormone is known to exist as an intact hormone, or nicked hormone (hormone with peptide bond cleavages in its β subunit) and fragments of the hormone in urine. The array of hLH-derived molecules in urine is likely to vary with the physiology of the individual when the urine is sampled, i.e. time of the menstrual cycle. Measurement of each of these molecular species is not currently possible (Ward et al., 1989). Some of the antibodies reported here provide immunological tools to extract and examine the nature of these forms of hLH. The measurement of hLH in serum by monoclonal antibodies is also complicated by the occurrence of anomalous circulating forms of hLH in the same individuals (Petterson et al., 1991, 1992).

The cloning and selection of monoclonal antibodies to hLH was quite different from earlier experiences with hCG antibodies. The majority of antibodies resulting from immunization with hCG were directed to site II (FIG. I) on the β subunit, which is a site present on both free β subunit and on the dimeric hormone. Other investigators have had a similar experience with hCG (Norman et al., 1985; Schwarz et al., 1986). Table 1 illustrates the differences observed with hLH immunization. In this case, most of the antibody-producing cells from the hLH-immunized animal were directed to site III, intact hLH (41.7%), and not to hLH/hLH β (21.7%, the site II antibodies). It was found that less than 6% of the cells produced antibody directed to both free α subunit and dimeric hormone (Site V). In contrast, other groups have found much higher percentages of such antibodies. Soos & Siddle (1983), who also immunized mice with intact hLH, found that 50% of the cells producing antibody were directed to α subunit. Alonso-Whipple et al. (1988) also found that 5% of the antibodies to hLH were directed primarily to the α subunit. Berger et al. (1988) found that over 65% of the antibodies developed to hFSH were directed to the α subunit.

As described below, selection of antibodies to hLH was directed towards obtaining a wide array of antibodies which would bind to different regions of the hormone. The first step in this selection process was the screening of antibody-producing lines with a variety of labeled tracers. The second step was the application of the cooperativity effect (Ehrlich et al., 1982, 1985) used to select antibodies which would bind simultaneously with another antibody with enhanced combined binding affinity (Ehrlich et al., 1985). This procedure developed from the observation that two simultaneously-binding antibodies could interact in a fashion to raise the binding affinity above that expected for each ligand-antibody reaction itself (O'Connor et al., 1988). During selection of antibodies, this effect of dual binding antibodies is observed during the course of titrating cell supernate with radiolabeled tracers. Addition of a second antibody which binds cooperatively with the first antibody, raises the binding of the radiolabeled tracer to above the 100% binding value observed with a single antibody. It is also possible for two antibodies to bind to the ligand simultaneously but not in a cooperative fashion. Such antibodies would not be detected by this method (O'Connor et al., 1988). The third step in selection is the examination of cloned lines by the IRMA technique (Table 4) and the identification of antibodies useful for measurement systems and for epitope mapping. This sequence of procedures resulted in the immunological map presented in FIG. 1.

Seven distinct antibody-binding sites were identified on the surface of hLH (FIG. 1). Earlier, using similar strategies to map hCG, only five sites were identified, of which one was unique to the β COOH-terminal region (Ehrlich et al., 1982, Krichevsky et al., 1988). Immunological mapping of hLH by Alonso-Whipple and colleagues (1988) found six sites on α and two on β subunits. Other investigators have found various numbers of distinctly different sites', the number depended on the technique employed to assess simultaneous binding. For example, using strictly solid-phase rather than a combination of both liquid phase and solid phase screening, Soos and Siddle (1983), Norman et al. (1985) and Schwarz et al. (1986) identified many more sites on each hormone. Solid phase screening alone seems to either create more sites (for example, binding to the solid phase may alter the molecules's confirmation and induce the formation of new epitopes) or make overlapping sites appear more distinct than they do in the liquid phase system due to the higher local concentrations of reagents. It is preferred to use both methods of epitope mapping, as described herein, for a better representation of discrete sites. Genetic techniques, which allow cutting and splicing of the hormones, provide a promising new site-mapping strategy which can give a more precise identification of the amino acids involved in the binding sites (Campbell et al., 1988; Moyle et al., 1990).

Table 2 and FIG. 1 summarize the different sites found on hLH from these initial studies. Table 2 is a guide to the nomenclature and site specificities of the antibodies described herein. Antibody map sites, which are analogous to those of hCG, are sites II, V and III. The antibodies to these site III (B405, B406) sites will bind at the same time as the other dimer-directed antibody of site VII (A407), and thus two dimer-directed antibodies can be used in a single assay which potentially provide greater specificity than can be obtained with the use of one alone. The data from the IRMA-type assays (Table 4) show how different combinations of capture and detection antibodies can be used to measure specifically a variety of antigens present together with immunologically related molecules in complex solutions. Two interesting observations deserve further comment:

First, the combination of B408 as capture and B409 as detection antibodies provides a comprehensive assay for intact hormone, β subunit and potential fragments of the β subunit suitable for both urine and serum. B408 captures both intact hormone and β subunit, while B409 detects both forms with high specificity and sensitivity.

Second, the change in specificity of B409 between liquid phase and solid phase assays deserves comment, especially in relation to clonal selection methodology. B409 will recognize only free hLHβ subunit in liquid phase assay, while in the IRMA format it recognizes hCG, hCG and hLH as either capture or detection antibody, although it always binds preferentially to hLHβ. There are two kinds of interaction that may alter antibody specificity. A solid phase bound antibody (capture antibody) may alter presentation of a ligand to a second detection antibody. For example, Rebois showed that the binding of an antibody (generated to native hormone) could change the shape of biologically inactive deglycosylated hormone so that biological activity was restored (Rebois & Fishman, 1984). Alternatively, binding of one antibody to a ligand may cause a distal conformation change in the ligand which alters binding of a second antibody to the ligand. The latter effect is exhibited in liquid phase assays or solid phase or both. It is possible that such effects alter the specificity of the antibody, and thus are responsible for the increased cross-reaction with the intact hLH and hCG antigens. Use of liquid phase screening permitted selection of antibody B409 for cloning. Using only a solid phase selection scheme would have made it seem that this antibody was not at all specific and it would not have been selected for further study (Vaidya et al., 1985).

II. Development, Characterization, and Application of Monoclonal Antibodies to the Native and Synthetic βCOOH-Terminal Portion of Human Chorionic Gonadotropin (hCG) that Distinguish Between the Native and Desialylated Forms of hCG Abstract Although the pregnancy hormone hCG has been extensively mapped immunochemically, few monoclonal antibodies have been produced to the unique COOH-terminal region of its β-subunit (βCTP). The development and characterization of five such monoclonal antibodies are now reported. Three of these antibodies were developed to the synthetic peptide analog of the hCGβ-(109–145) region coupled to diphtheria toxoid, and two antibodies to a conjugate of bovine thyroglobulin and the peptide hCGβ-(115–145) prepared from hCG with its carbohydrate moieties intact. The monoclonal antibodies raised against the synthetic peptide bound hCG, desialylated hCG, and synthetic peptide to a similar extent, whereas antibodies generated to the natural hCG peptide did not bind to the synthetic peptide analog of the COOH-terminal peptide (βCTP) region or to desialylated hCG. These new monoclonal antibodies could distinguish between native and desialylated hCG in liquid phase immunoassays as well as by Western blots. They are highly specific reagents for such Western blotting and were used for studies of a crude human pituitary gonadotropin preparation to demonstrate that it contained intact hCGβ without the internal peptide bond cleavages found in the subunit present in human blood and urine. Competition experiments using combinations of monoclonal antibodies and rabbit anti-βCTP antiserum demonstrated that two epitopes exist within the β-(115–145) region of hCG, one of which depends on the presence of carbohydrate. In summary, the new monoclonal hCG βCTP antibodies reported here can (1) discriminate between native and desialylated hCG, (2) identify hCG and nicked hCG on Western blots, (3) provide an immunoaffinity purification tool for hCG, and (4) bind to two distinct epitopes on the βCTP.

Introduction

HCG is a glycoprotein hormone produced by the trophoblast early in pregnancy which serves to maintain the steroid secretion of the corpus luteum (1). It is the sole member of the glycoprotein hormone family produced by the placenta (1). The other glycoprotein hormones, FSH, TSH, and LH, are all synthesized within the pituitary. Immunochemical evidence demonstrates that a small amount of hCG is produced by both human adult and fetal pituitaries (2–4). Recently, a report has appeared that mRNA for hCG has also been identified in human pituitary tissue (5). hCG shares a common α-subunit with the other glycoprotein hormones, whereas the β-subunits confer receptor target specificity to each hormone. hCG is highly homologous to hLH in amino acid sequence, and both hormones bind to the same receptor (1,6). The chief structural difference between them is the hCG COOH-terminal peptide β-(115–145) (βCTP), which contains four O-serine-linked carbohydrate moieties. This region of the hCG β-subunit, which is not present in hLH, has been employed by various investigators for generation of hCG-specific antisera that can measure the hormone accurately even in the presence of high concentrations of hLH (6).

Work has previously concentrated on the development of rabbit antisera to carrier-conjugated forms of the βCTP isolated from native or desialylated hCG (7,8). Natural carbohydrate-containing peptides generate rabbit antisera of higher affinity to hCG than antisera prepared against synthetic peptide conjugates (9). However, such immunogens frequently produced antisera that required both the peptide and carbohydrate portions of the βCTP region for efficient binding to hCG (7,9). Those antisera have had applications in monitoring patients with hCG-producing tumors, who excrete hCG in which sialic acid is reduced or absent (10, 11). Because of the disadvantages of rabbit polyclonal antisera, such as limited supply and variability, monoclonal antibodies were developed.

Although a number of polyclonal antisera have been developed to synthetic analogs of the hCGβ COOH-terminal region, few monoclonal antibodies have been developed, presumably as a consequence of the peptide's low antigenicity in mice (12, 13). Because of their unique specificity, monoclonal antibodies to the βCTP region of hCG are particularly useful for purification and visualization of hCG in such biological matrices as blood, urine, and tissue extracts.

Five monoclonal antibodies raised against the hCG βCTP region were generated and characterized. Three were produced using synthetic peptide conjugated to diphtheria toxoid, as had been employed in a contraceptive vaccine in primates (14–16). The other two monoclonal antibodies were produced in response to an immunogen derived from the carbohydrate-containing peptide, isolated from hCG and conjugated to bovine thyroglobulin. Both antibodies to a carbohydrate-containing antigen displayed a requirement for carbohydrate antigen, which included the sialic acid (as well as the peptide backbone) for proper recognition of hCG, as in some of the rabbit antisera developed earlier (9).

Materials and Methods

Production of Antibodies

Antibodies to the synthetic peptide analog hCGβ-(109–145) conjugated to diphtheria toxoid (DT). hCGβCTP:DT conjugate was prepared according to the method of Lee et al. (15, 16) and contained 25 peptides/100 kilodaltons DT. The synthetic adjuvant, nor-MDP (CGP 11637, N-acetyl-nor-muramyl-l-alanyl-b-isoglutamine) was prepared at Ciba-Geigy Ltd. (Basel, Switzerland). Squalene and Arlacel A were purchased from Sigma Chemical Co. (St. Louis, Mo.) and mixed 4:1 (wt/wt), respectively. Details of the preparation of the immunogen adjuvant and vehicle into an emulsion have been described previously (15, 16). Briefly, hCGβ-CTP:DT was mixed with nor-MDP (2:1, wt/wt), dissolved in saline, and emulsified with an equal volume of squalene-Arlacel A (4:1. wt/wt).

The immunization protocol used 100 μg immunogen injected into BALB/c Byl mice, followed by booster injections at 3- to 4-week intervals using the same material and dose. Before spleen excision and fusion, a boost of 200 μg conjugate in saline was administered by iv without squalene-Ariacel A. Supernates from microtiter plates containing cells from the fusion were screened by liquid phase RIA with iodinated hCG, and the cells from three positive wells were cloned.

Antibodies to carbohydrate-containing hCGβ COOH-terminal peptide. The immunogen was hCGβ-(115–145) (prepared from natural hCG), conjugated to bovine thyroglobulin by a modification of the method of Lee et al (14). It was necessary to add a thiol group to hCGβ-(115–145) to conjugate it to a carrier with its COOH-terminal region projecting outward form the carrier surface. This was accomplished as follows. hCGβ-(115–145) (2.5 mg) was dissolved in 0.5 ml 0.1. M sodium borate, pH 9. N-Succinimidyl 3-(2-pyridyldithio)propionate (SPDP; Pierce Chemical Co., Rockford, Ill.; reagent T21557; 2 mg) was dissolved in 200 μl dimethylsulfonyl-fluoride, added to the peptide, and incubated for 1 h at ambient temperature. The solution was then separated by gel filtration on Sephadex G-25 (PD10 column, Pharmacia, Piscataway, N.J.) in 0.1 M ammonium bicarbonate. The void volume was lyophilized. The carrier thyroglobulin was derivatized for conjugation as follows: bovine thyroglobulin (3 mg; Sigma Chemical Co.) was dissolved in 600 μl 0.05 M sodium phosphate, pH 7.2 to which were added 150 μl of a solution of m-maleimidobenzyl-n-hydroxysuccinimide ester (reagent 22310; Pierce Chemical Co.) at 6 mg/ml in dimethylformamide and stirred at ambient temperature for 30 min. This solution was gel filtered on Sephadex G-25 on a PD-10 column (Pharmacia) in 0.05 M sodium phosphate, pH 6. Simultaneously, the derivatized SPDP-βCTP was incubated with 30 mg dithiotreitol (to release the thiol group from the SPDP portion) in 600 μl 0.05 M sodium phosphate, pH 7, for 1 h at 37 C. and gel filtered on Sephadex G-25 in the same buffer. The peptide void volume peak from the column was mixed immediately with the derivatized thyroglobulin. The pH was adjusted to 7.5, and the peptide-carrier was incubated overnight. The solution was then concentrated to 0.5 vol on a Savant Speed-Vac (Hicksville, N.Y.) and fractionated on a tandem set of Superose-12 columns (Pharmacia) in 0.05 M ammonium bicarbonate. Amino acid analysis of the carrier-conjugate indicated that the molar conjugation ratio was greater than 20:1 of peptide to carrier (20 peptides/molecule of carrier).

The immunization protocol for mice was similar to that described for the synthetic peptide immunogen, except that a low dose of antigen (10 μg) was employed. The boost injection before fusion was reduced to 20 μg. Supernates from wells containing cells from the fusion were screened by liquid phase RIA with radiolabeled hCG as well as by enzyme-linked immunosorbent assay with hCG, hCGβ, hCGβCTP, RCMβ, desialylated hCG, and desialylated hCG RCMβ. Cell fusion and hybridoma screening process were described in detail previously (17).

Gel Electrophoresis

Sodium dodecyl sulfate (SDS)-polyacrylamide gels were prepared according to the procedure described by Laemmli (18). The stacking and resolving gels each contained 0.1% SDS (BDH, Carle Place, N.Y.); acrylamide (BDH) stock was used at a concentration of 30% acrylamide-0.8% bisacrylamide (Bio-Rad, Melville, N.Y.). Prestained SDS-polyacrylamide gel electrophoresis standards (Gibco, Grand Island, N.Y.) were diluted 1:2 in 2×sample buffer {1×= 0.0625 M Tris-HCl (pH 6.8), 2% SDS, 10% glycerol, and 0.001% bromophenol blue}. Approximately 70 pmol protein were diluted in sample buffer at 4° C. Gels (0.75 mm thick) underwent electrophoresis for 46–60 min at constant current (20 mamp) at 4° C. (19). For reduced gels, the sample buffer included 5% β-mercaptoethanol.

Immunoblotting

The crude gonadotropin preparation was extracted from acetone-dried human pituitaries (20). After electrophoresis, the gel was soaked for 5 min in transfer buffer (0.025 M Tris base, 20% methanol and 0.2 M glycine). The electrophoretic transfer of the proteins in the gel to nitrocellulose was accomplished according to the methods of Towbin et al. (21) and Burnette (22) at 100 V for 1 h. The transfer chamber was kept cold by a circulating water pump set at 12° C.

Protein Visualization

The nitrocellulose paper was first incubated in 5% BSA in 0.01 M Tris-HCl and 0.15 M NaCl, pH 7.6 (BSA-TBS), for 45 min at 37 C and then incubated with the primary antibody (βCTP 103) in BSA-TBS overnight, with rotating, at room temperature. The nitrocellulose was washed in TBS for 1 h with four changes of TBS buffer. The secondary antibody, peroxidase-conjugated rabbit antimouse antibody (Accurate Biochemical, Westbury, N.Y.), at a dilution of 1:300 in βSA-TβS, was incubated with the nitrocellulose, with rotating, at room temperature for 3 h. The nitrocellulose was again washed with TβS as described above. The peroxidase-conjugated antibody was visualized by adding a mixture of 60 μl 30% $H_2O_2$ in 100 ml TβS and 60 mg 3,3'-diaminobenzidine tetrahydrochloride (Bio-Rad) in 20 ml cold methanol. The staining reaction was stopped by rinsing the nitrocellulose in deionized water.

Liquid Phase RIA Competition Between Monoclonal and Polyclonal Antibodies

Liquid phase immunoassay competitions between polyclonal and monoclonal antibodies were conducted as follows. Radiolabeled hCG was used as a tracer. Each tube contained 100 μl tracer, 200 μl buffer, 100 μl rabbit polyclonal antibody, and 200 μl mouse monoclonal antibody competitor. After incubation for 16 h in the cold, sheep anti-rabbit immunoglobulin was added to precipitate the polyclonal antibody bound to hCG tracer. The counts bound represented only the binding of the rabbit antibody to hCG in the presence of the competing mouse monoclonal antibodies.

Results

All immunized animals developed measurable binding titers of radiolabeled hCG in their sera. However, a number of spleen fusions from mice with high serum titers failed to produce cells secreting antibodies that could be measured by binding to radioiodinated hCG in a liquid phase system. A fusion of the spleen from one mouse immunized with synthetic βCTP vaccine resulted in the production of CTP-(101–103). Because of the problems in selecting CTP antibodies solely with liquid phase screening, the fusion of the spleen cells from one mouse immunized with native peptide was screened by both liquid and solid phase techniques. This dual strategy allowed identification of a number of binding properties of interest. Two cell lines derived form immunization with native β-(115–145), which were positive in both liquid and solid phase binding of hCG and hCGβ, were selected and cloned, and are reported here as CTP-140 and CTP-105. No other supernate from this fusion bound radiolabled hCG in the liquid phase, but many bound hCG in a solid phase format, suggesting that most antibodies to this immunogen were of low affinity ($<10-7$ liters/M) (23) or, alternatively, attached to determinants formed on hCG when it binds to a plate surface. Thus, herein, only those antibodies that would be useful in both solid and liquid phase immunoassays are described.

Figure 4:
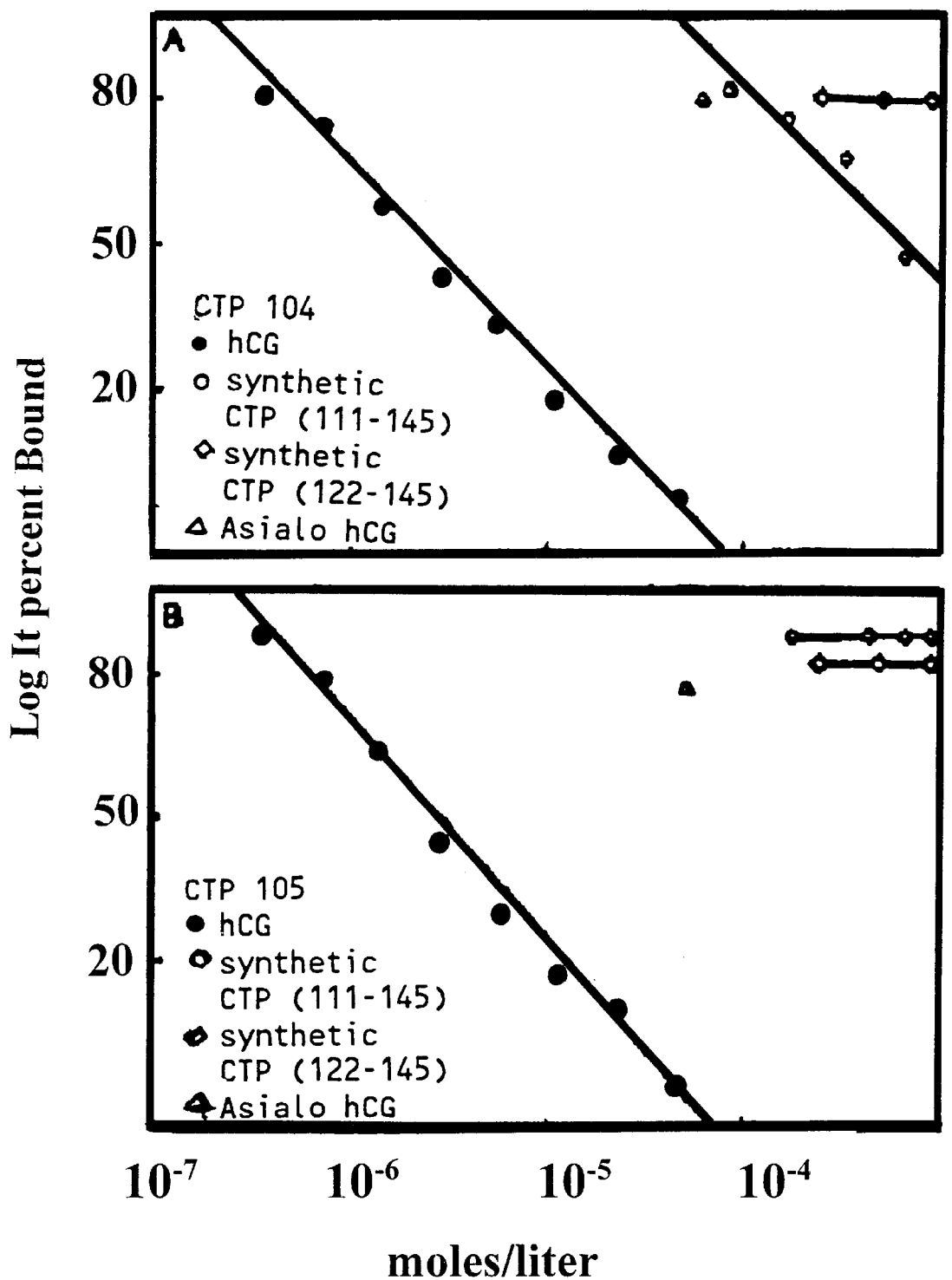

The affinities of all five of the monoclonal antibodies to hCG and hCGβ appear in Table 6, and all are of the order of $10^8$ liters/M. When dose-response studies were performed to compare binding to hCG with hCGβ synthetic peptide analogs, it was evident that two different types of monoclonal antibodies had been produced. As illustrated in FIGS. 7A and 7B, both hCG and synthetic hCGβ-(111–145) competed equally well with radiolabeled hCG for binding to each antibody generated to the synthetic peptide immunogen (CTP-101, CTP-102, and CTP-103). However, the pattern of competition was quite different in the case of antibodies CTP-104 and CTP-105, which were generated against carbohydrate-containing hCGβ COOH-terminal peptide. Both antibodies displayed a distinct preference for the sialic acid-containing competitors (FIG. 4). Synthetic peptides or desialylated hCG competed either very weakly or not at all at dose ranges as high as 3 orders of magnitude above the doses of native hCG (FIG. 4). Synthetic β-(111–145) competed slightly with CTP-104, but not with CTP-105 at similar high doses, which indicates subtle differences in the epitopes recognized by these two antibodies.

TABLE 6

| | | | Competitors | | | |
|---|---|---|---|---|---|---|
| Immunogen | Antibody | Tracer | hCG | hCGβ | Asialo hCG | Synthetic β-(111–145) |
| Synthetic β-(109–145) | CTP 101 | hCG hCGβ | $5 \times 10^8$ NT | NT $5 \times 10^8$ | $5 \times 10^8$ NT | $5 \times 10^8$ NT |
| Synthetic β-(109–145) | CTP 102 | hCG hCGβ | $3 \times 10^8$ NT | NT $5 \times 10^8$ | $3 \times 10^8$ NT | $3 \times 10^8$ NT |
| Synthetic β-(109–145) | CTP 103 | hCG hCGβ | $2 \times 10^8$ NT | NT $5 \times 10^8$ | $2 \times 10^8$ NT | $2 \times 10^8$ NT |
| Native β-(109–145) | CTP 104 | hCG hCGβ | $2 \times 10^8$ $1 \times 10^8$ | $1 \times 10^8$ $1 \times 10^8$ | ND NT | $1 \times 10^{8*}$ NT |
| Native β-(109–145) | CTP 105 | hCG hCGβ | $1 \times 10^8$ $1 \times 10^8$ | $2 \times 10^8$ $2 \times 10^8$ | ND NT | ND NT |

Figure 5:
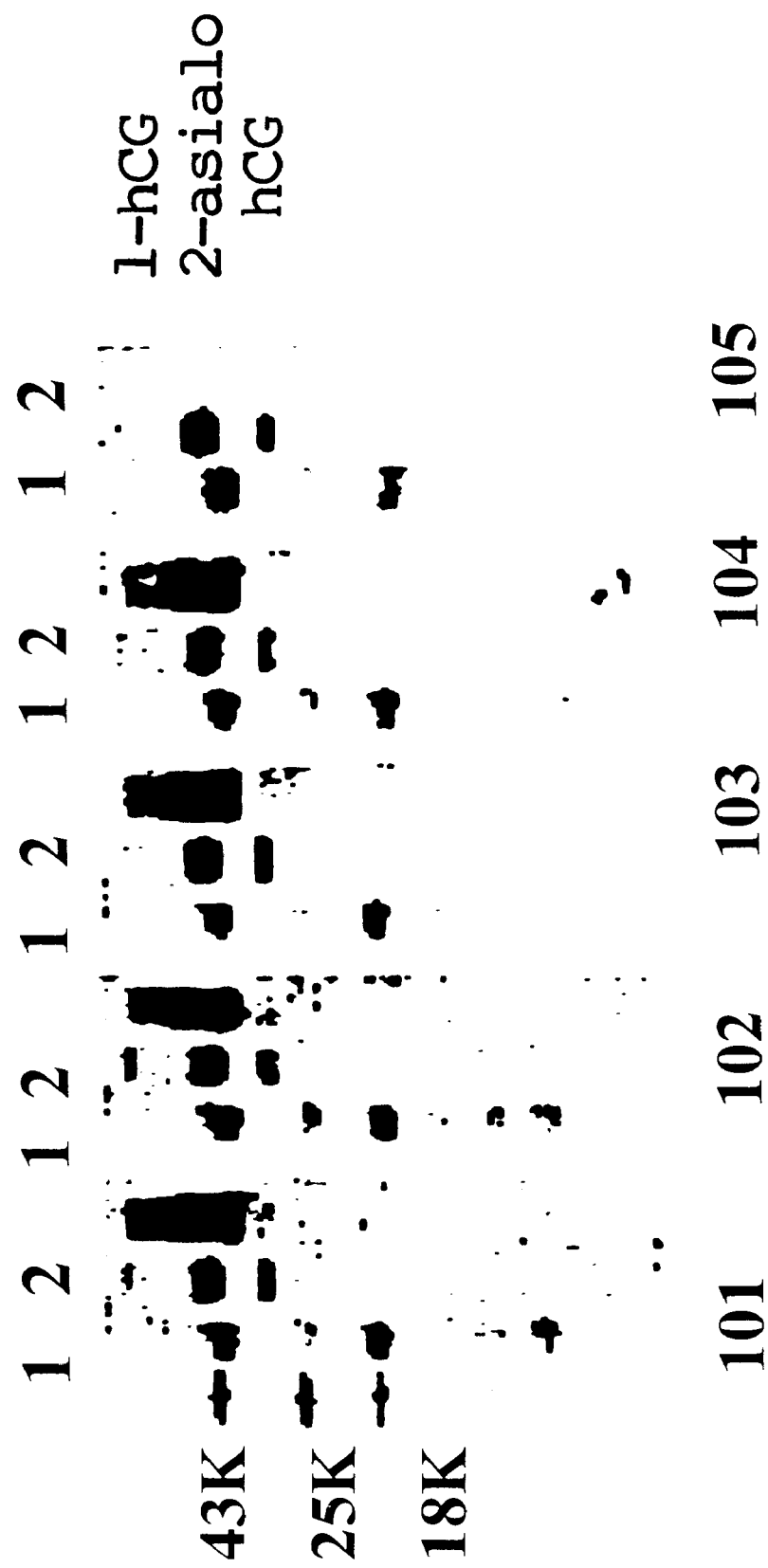

Affinity constants are given in liters per molar concentration.
NT, not tested; ND, not detected.
*Estimate The increased specificity and homogeneity of monoclonal antibodies render them more advantageous than polyclonal antibodies for immunoblotting and immunoaffinity procedures. Therefore, five monoclonal antibodies were tested for recognition of hCG and desialylated hCG on immunoblots and found that under nonreducing conditions, CTP-104 and especially CTP-105 could differentiate native from desialylated hCG (FIG. 5). The band below the intact hCG represents a small quantity of dissociated hCG β-subunit (10%).

Figure 6:
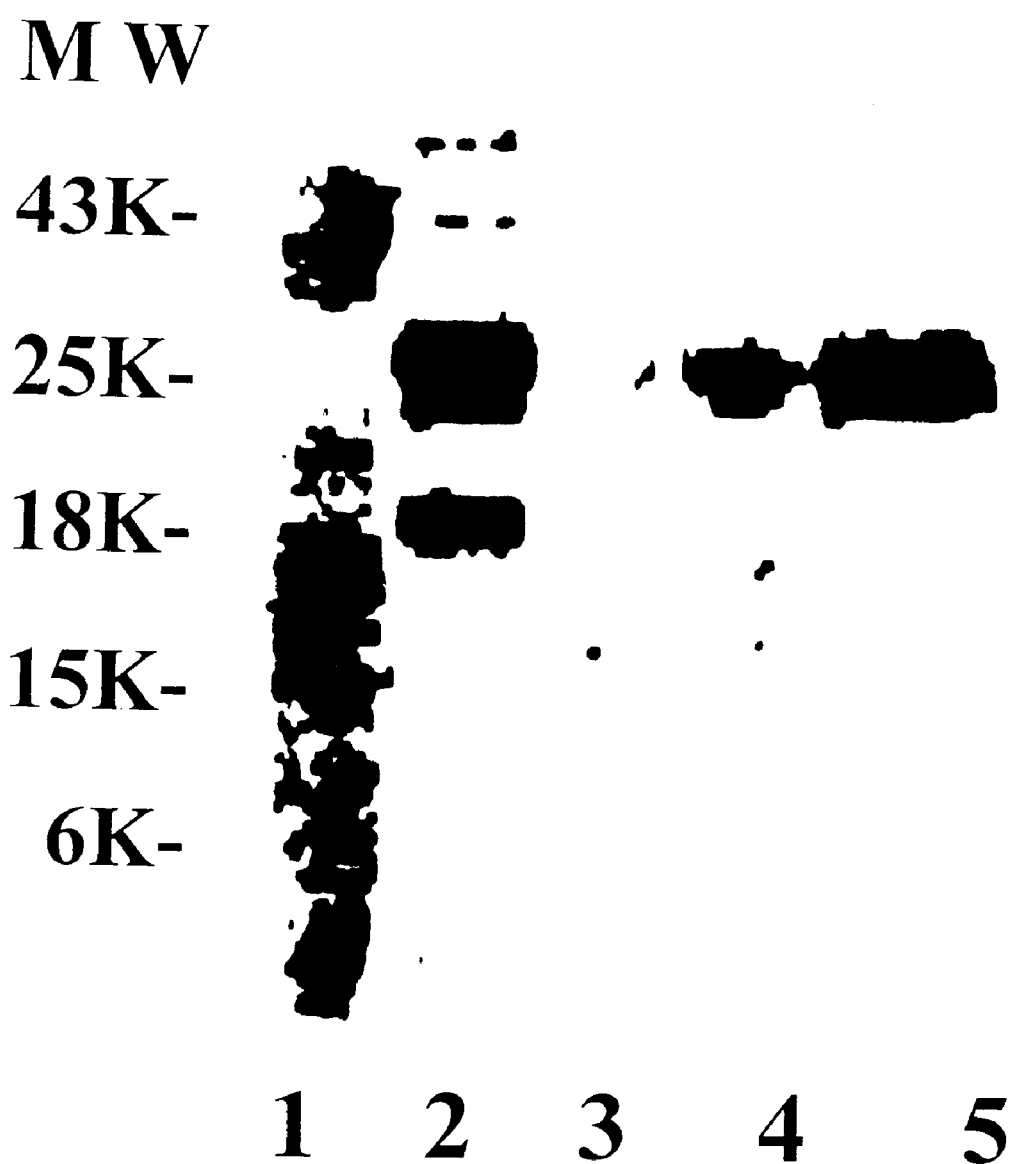

Another example of the utility of the monoclonal βCTP antibodies for blotting was obtained on a reduced and boiled sample of a crude gonadotropin extract from acetone-preserved human pituitary glands (FIG. 6). There was clear evidence of a βCTP-staining band at the position of intact hCGβ (lanes 3–5). Little, if any of the lower 20,000-kilodalton (kDa) band apparent in standard hCGβ (24, 25) shown in lane 2 was present in the pituitary hCGβ. The intact hCGβ appeared as approximately 33 kDa, whereas the peptide at 20,000 kDa represented β-45 or -(48–145) (lane 2). This lower band in the hCG standard was a result of peptide bond cleavages present in urinary preparations of hCG (24, 25). Thus, the hCGβ extracted from acetone-preserved pituitaries, which is reactive to antibodies specific for the C-terminal peptides, appears to contain intact β-subunit chains.

Competition Between Monoclonal and Polyclonal Antibodies for Sites on the hCGβ COOH-terminal Region The monoclonal antibodies CTP-101, CTP-102, and CTP-103 appeared to be similar in specificity to the rabbit antibodies R525 and R529 that had been developed previously (8). Those rabbit antisera reacted well with both sialic acid-containing and desialylated hCG(8). In contrast, CTP-104 and CTP-105 were similar in specificity to rabbit antiserum R561, which preferentially bound to sialic acid-containing hCG(9). The hypothesis was tested that R561 bound to the same site as did antibodies CTP-104 and CTP-105. FIGS. 7A and 7B show dose-response curves that support this hypothesis. When CTP-103 was used as a competitor in a liquid phase assay with R561 and hCG tracer, it did not compete for binding of radiolabeled hCG with the rabbit antiserum for hCG. In contrast, monoclonal antibodies CTP-104 and CTP195 did compete with R561 in binding to hCG (FIG. 7A). Titrations of CTP-103 and CTP-104 with hCG tracer in the presence of R561 and using an antimouse immunoglobulin to separate free from bound material produced similar binding curves (data not shown). However, when rabbit antiserum R525, which binds to both sialic acid-containing and desialylated hCG, was used in a similar study, it was found that monoclonal antibodies CTP-103, CTP 104, and CTP-105 each competed with the rabbit antibody (FIG. 7B), suggesting that the R525 polyclonal antisera contained antibodies that bind to sites overlapping the epitopes of all the monoclonal βCTP antibodies.

Discussion

The COOH-terminal region of hCG has been extensively employed for development of antibodies that will specifically measure hCG in the presence of hLH, the latter of which lacks this epitope (1, 6). Unfortunately, this region of hCG is much less immunopotent than the remainder of the molecule and only elicits antibodies when used as a carrier-conjugated immunogen. Antibodies that react with this region have never been reported to result from immunization with the whole hormone or free hCGβ-subunit.

Although there are many potential applications for monoclonal antibodies to the hCGβ COOH-terminal peptide, few such antibodies have been developed (12, 13). Again, this is due to the low antigenicity of this region. It is unusual for rabbits to produce high affinity antisera to the βCTP (7, 9, 26). Chen et al. (26) have reviewed these problems in detail.

On the basis of past experiences with such polyclonal antisera, both synthetic peptide and a native hCG-derived peptide immunogen were employed for this study. The first immunogen, a synthetic peptide analog, was the same type of preparation used to induce circulating antibodies capable of preventing pregnancies in primates and humans (27). The immunogen generated antibodies of moderate affinities in mice. All three of the cloned antibodies recognized hCG and synthetic peptide equally well on a molar basis, indicating no influence of carbohydrate content on binding. In contrast, the two antibodies generated by the natural carbohydrate-containing hCGβ peptide both exhibited a requirement for the carbohydrate and the peptide chain of the COOH-terminal region for recognition of ligand. Polyclonal antibodies developed to this type of immunogen were similar in specificity (9), suggesting that this type of immune response is likely to be common among rabbits and mice. Despite the use of both types of immunogens, which contained high molar ratios of hapten to carrier protein, with the COOH-terminal end of each peptide projecting outward, very few hybridoma cells produced antibodies of sufficient affinity to be measured in liquid phase assay screening. For example, although high titer binding of radiolabeled hCG was observed in liquid-phase assays by the sera of mice immunized with both synthetic and natural peptide immunogens, the desired PCTP antibody-secreting cells could not be readily identified. Perhaps the high titers to hCG in the sera reflected the simultaneous binding of two antibodies to the hCG βCTP region, with a resultant enhancement of affinity for hCG (23, 28). A large number of low affinity antibodies may give the appearance of high hCG binding in the serum, whereas very few high affinity antibodies are actually present. In any case, because so few hybridoma cells produced detectable antibodies to hCG, cloning of these antibodies was difficult and explains why so few such antibodies have been reported in the literature.

The five hCGβ COOH-terminal binding monoclonal antibodies represent two types with complementary specificities. Antibodies of the first type react with all forms of hCG containing βCTP, regardless of carbohydrate differences. Antibodies of the second type display greater sugar specificity and can be used to monitor alterations of the carbohydrate in this region, as in the hCG secreted by patients with certain trophoblastic malignancies (10, 11).

These new monoclonal antibodies are capable of identifying a band containing intact hCG β-subunit in Western blots of reduced crude pituitary extracts. The observation that hCGβ exists in the human pituitary has been reported previously (2–4). hCG in both urine and blood appears to contain peptide bond cleavages within hCGβ between residues 44–45 and/or 47–48 (24, 25). It is unusual to find an individual producing hCG without such cleavages (24). The finding that the hCG in pituitary appears intact compared to that found in serum and urine has not previously been noted and was unexpected in view of the reports of the occurrence of nicked pituitary hLH (29, 30). Pituitary tissue is rich in protease activity, and one might have anticipated that much of the hCG would have been internally nicked and that much or all of the βCTP peptide would also have been cleaved free from hCG by protease activity.

The findings herein indicate that acetone preservation of pituitary glands does preserve pituitary hCG intact. The fact that this method of tissue preservation inhibits the activity of proteases during storage of the tissue may explain this absence of nicking. However, once the pituitary powder is returned to the aqueous environment, proteases have been shown to be active in producing nicks in hLH, especially after subunit dissociation (30). Because the β-COOH-terminal peptide of placental hCG is so easily cleaved from the hormone by proteases (31), the presence of intact hCGβ chains further attests to the limited protease activity in the preserved glands.

Two monoclonal antibodies, CTP-104 and -105, and the polyclonal antiserum R561 bind to the same or overlapping sites on the hCG βCTP region. In contrast, CTP-103 does not compete with R561 and, thus, binds to a different site on the βCTP region. CTP-103, CTP-104, and CTP-105 all compete with rabbit antiserum R525 showing that they have overlapping binding sites with this antiserum, which binds both sialic acid-containing and desialylated forms of hCG (8). CTP-104 and CTP-105 bind to more complex epitopes than CTP-103, which was made to a synthetic analog. The epitopes recognized by the monoclonal antibodies CTP-104, CTP-105 and the polyclonal antiserum R561 contain both the polypeptide chain as well as sialic acid-terminating sugar moieties. Monoclonal antibodies CTP-101, CTP-102, and CTP-103 are similar to R525 and R529 antisera in recognizing the polypeptide backbone of this region regardless of its carbohydrate content. Yet, CTP-104 and CTP-105 must bind to a similar region as R525 antiserum because they compete with R525. One possible interpretation is that at relatively high concentrations both CTP-104 and -105 bind with low affinity to the hCG peptide backbone without sialic acid and are capable of displacing R525 from radiolabeled hCG.

Because R525 is polyclonal, its binding to hCG reflects the reaction and possibly cooperativity associations (23, 28) of a variety of antibodies. In contrast, CTP-103 cannot displace R561 from radiolabeled hCG, indicating that the affinity of R561 for sialic acid-containing hCG is much higher than that of CTP-103.

The two types of monoclonal antibodies to the unique COOH-terminal peptide of hCG β-subunit, each binding to a different unique CTP epitope, have complementary specificities and are highly useful in laboratory research procedures as well as in clinical assays. It may be possible to use these antibodies to extract particular forms of hCG from blood and urine without interference by related proteins.

REFERENCES

Section I of Experimental Details

Akar, et al., J. Clin. Endocrinol. Metab. 66:538–545 (1988).
Alonso-Whipple, et al., Endocrinology, 123:1854–1860 (1988).
Armstrong, et al., J. Clin. Endo. Metab., 59:867–874 (1984).
Berger, et al. Endocrinology., 123: 2351–2359 (1988).
Campbell, et al. Placental Protein Hormones, Mochizuki, et al. (eds.), Elsevier Excerpta Medica: Amsterdam-New York Oxford pp. 123–132.
Canfield, et al., Environ. Health Perspec., 74:57–66 (1987).
Chow, et al., J. Appl. Biochem., 7:114–121 (1985).
Coller, et al., Hybridoma, 2:91–95 (1983).
Ehrlich, et al., Am. J. Reprod. Immunol. Microbiol., 8:48–54 (1985).
Ehrlich, et al., Methods in Enzymology Hormone Action Part I Peptide Hormones, Birnbaumer, et al. (eds.) Academic Press, 109: 638–655.
France, J. T., Recent Advances in Obstetrics and Gynecology, Churchill Livingstone: Edinburgh and New York, pp. 215–239.
Hartree, et al., J. Endo., 96:115–126 (1983).
Hunter, et al., Ann. Clin. Biochem., 21:275–283 (1984).
Hussa, et al. The Clinical Marker hCG, Praeger Publishers, New York (1987).
Kerin, et al., Lancet, 11:430–431 (1990).
Krichevsky, et al., Endocrinology, 123:584–593 (1988).
Krichevsky, et al., Endocrinology, 128:1255–1264 (1991).

Lichtenberg, et al., Horm. Metabol. Res., 14:39–45 (1982).
Livesey, et al., J. Endocrinology, 98:381–384 (1983).
Lloyd, et al., Am. J. Obstet. Gyn., 160:1370–1375 (1989).
Moyle, et al., J. Biol. Chem., 265:8511–8518 (1990).
Norman, et al., J. Clin. Endo. Metab., 61:1031–1038 (1985).
O'Connor, et al., Cancer Res., 48:1361–1366 (1988).
Odell, et al., J. Clin. Invest., 46:248–255 (1967).
Odell, et al., Clin. Chem., 33:1603–1607 (1987).
Petterson, et al., Clin. Chem., 37:1745–1748 (1991)..
Petterson, et al., J. Clin. Endo. Metab., 74:164–171 (1992).
Pierce, et al., Ann. Rev. Biochem. 50:465–495 (1981).
Rebois, et al., J. Biol. Chem., 259:8087–8090 (1984).
Scatchard, et al. Ann. NY Acad. Sci., 51: 660–672 (1949).
Schwarz, et al., Endocrinology, 118:189–197 (1986).
Singh, et al., Fertil. Steril., 41: 210–217 (1984).
Soos, et al., Clin. Chim. Acta., 133:263–274 (1983).
Soos, et al., J. Immunol. Meth., 73:237–249 (1984).
Umapathysivam, et al., Europ. J. Obstet. Gyn. Reprod. Biol., 19:31–35 (1985).
Vaidya, et al., Hybridoma, 4:271–276 (1985).
Vaitukaitis, et al., Am. J. Obstet. Gyn. 113:751–758 (1972).
Ward, et al. Microheterogeneity of Glycoprotein Hormones, Keel, et al. (eds.) CRC Press, New York, pp. 2–22.
Wilcox, et al., Env. Health Perspec., 75:29–35 (1987).
Wilcox, et al., N. Engl. J. Med., 319:189–194 (1988).

Section II of Experimental Details

1. Pierce, J. G. et al., Annu. Rev. Biochem. 50:465–495 (1981).
2. Chen, H. C. et al., Proc. Natl. Acad. Sci. USA 73:2885–2889 (1976).
3. Hoermann, R. et al., J. Clin. Endocrinol. Metab. 71:179–186 (1990).
4. Hammond, E. et al., J. Clin. Endocrinol. Metab. 72:747–754 (1991).
5. Van Strien, A. et al., Nucleic Acids Res. 17:5406 (1989).
6. Hussa, R. O., The Clinical Marker hCG, Praegar, New York (1987).
7. Birken, S. et al., Endocrinology 106:1659–1664 (1980).
8. Birken, S. et al., Endocrinology 110:1555–1563 (1982).
9. Birken, S. et al., Endocrinology 122:2054–2063 (1988).
10. Miztrochi, T. et al., J. Biol. Chem. 258:14126–14129 (1983).
11. Amr, S. et al., J. Clin. Invest. 71:329–339 (1983).
12. Belet, D. et al., Endocrinology 115:330–336 (1984).
13. Caraux, J. et al., J. Immunol. 134:835–840 (1985).
14. Lee, A. C. et al., Mol. Immunol. 17:749–756 (1980).
15. Stevens, V. C. et al., Am. J. Reprod. Immuno. 1:307–314 (1981).
16. Stevens, V. C. et al., Am. J. Reprod. Immuno. 1:315–321 (1981).
17. Krichevsky, A. et al., Endocrinology 123:584–593 (1988).
18. Laemmli, U. K., Nature 227:680–685 (1970).
19. Schlaff, S., Endocrinology 98:527–533 (1976).
20. Hartree, A. S., Academic Press, New York, 37:380–389 (1975).
21. Towbin, H. et al., Proc. Natl. Acad. Sci. USA 76:4350–4354 (1979).
22. Burnette, W. N., Anal. Biochem. 112:195–203 (1981).
23. Ehrlich, P. H. et al., Monoclonal antibodies to gonadotropin subunits. In: Birnbaumer, L., O'Malley B W (eds.) Methods in Enzymology, part I. Academic Press, New York, 109:638–655 (1985).
24. Kardana, A. et al., Endocrinology.129:1541–1550 (1991).
25. Birken, S. et al., Endocrinology 129:1551–1558 (1991).
26. Chen, S. C. et al., Limitations and problems of hCG-specific antisera. In: Segal., S J (eds) Chorionic Gonadotropin. Plenum Press, New York, pp. 231–252 (1980).
27. Jones, W. R., Lancet 1:1295–1298 (1988).
28. Ehrlich, P. H. et al., Am. J. Reproduc. Immunol. Microbiol. 8:48–54 (1985).
29. Ward, D. N. et al., Int. J. Peptide Protein Res. 27:70–78 (1986).
30. Hartree, A. S. et al., Mol. Endocrinol. 6:101–109 (1991).
31. Birken, S., J. Biol. Chem. 252:5386–5392 (1977).

What is claimed is:

1. A hybridoma cell line designated B152 (ATCC Designation No. HB-12467).

2. A monoclonal antibody produced by the hybridoma cell line of claim 1.

3. A hybridoma cell line designated B207 (ATCC Designation No. PTA-1626).

4. A monoclonal antibody produced by the hybridoma cell line of claim 3.

* * * * *